United States Patent
Baker, Jr. et al.

(10) Patent No.: US 9,839,685 B2
(45) Date of Patent: Dec. 12, 2017

(54) METHODS OF INDUCING HUMAN IMMUNODEFICIENCY VIRUS-SPECIFIC IMMUNE RESPONSES IN A HOST COMPRISING NASALLY ADMINISTERING COMPOSITIONS COMPRISING A NAONEMULSION AND RECOMBINANT GP120 IMMUNOGEN

(75) Inventors: James R. Baker, Jr., Ann Arbor, MI (US); Anna Bielinska, Ypsilanti, MI (US); Andrzej Myc, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1152 days.

(21) Appl. No.: 11/786,855

(22) Filed: Apr. 13, 2007

(65) Prior Publication Data

US 2008/0026988 A1    Jan. 31, 2008

Related U.S. Application Data

(60) Provisional application No. 60/791,758, filed on Apr. 13, 2006.

(51) Int. Cl.
*A61K 39/21* (2006.01)
*A61K 31/00* (2006.01)
*A61K 39/39* (2006.01)
*C07K 14/005* (2006.01)
*A61K 39/12* (2006.01)
*A61K 39/00* (2006.01)

(52) U.S. Cl.
CPC .............. *A61K 39/21* (2013.01); *A61K 31/00* (2013.01); *A61K 39/12* (2013.01); *A61K 39/39* (2013.01); *C07K 14/005* (2013.01); *A61K 2039/541* (2013.01); *A61K 2039/543* (2013.01); *A61K 2039/55555* (2013.01); *A61K 2039/55561* (2013.01); *A61K 2039/55566* (2013.01); *A61K 2039/55572* (2013.01); *C12N 2740/16122* (2013.01); *C12N 2740/16134* (2013.01)

(58) Field of Classification Search
None
See application file for complete search history.

(56) References Cited

U.S. PATENT DOCUMENTS

| | | |
|---|---|---|
| 4,481,188 A | 11/1984 | Apontoweil et al. |
| 4,895,454 A | 1/1990 | Kammleiter et al. |
| 5,039,688 A | 8/1991 | Lewis |
| 5,103,497 A | 4/1992 | Hicks |
| 5,510,104 A | 4/1996 | Allen |
| 5,547,677 A | 8/1996 | Wright |
| 5,549,901 A | 8/1996 | Wright |
| 5,571,531 A | 11/1996 | McDermott et al. |
| 5,618,840 A | 4/1997 | Wright |
| 5,662,957 A | 9/1997 | Wright |
| 5,700,679 A | 12/1997 | Wright |
| 5,716,637 A | 2/1998 | Anselem et al. |
| 5,942,237 A | 8/1999 | Gizurarson et al. |
| 5,951,988 A | 9/1999 | Littel-van den Hurk et al. |
| 5,961,970 A | 10/1999 | Lowell et al. |
| 6,015,832 A | 1/2000 | Baker et al. |
| 6,350,784 B1 | 2/2002 | Squires |
| 6,506,803 B1 | 1/2003 | Baker et al. |
| 6,558,695 B2 | 5/2003 | Luo et al. |
| 6,559,189 B2 | 5/2003 | Baker, Jr. et al. |
| 6,565,873 B1 | 5/2003 | Shefer et al. |
| 6,627,198 B2* | 9/2003 | Reed et al. ............... 424/190.1 |
| 6,635,676 B2 | 10/2003 | Baker, Jr. et al. |
| 7,314,624 B2* | 1/2008 | Baker et al. ............... 424/192.1 |
| 7,357,936 B1* | 4/2008 | Garcon ...................... 424/278.1 |
| 7,371,395 B2 | 5/2008 | Parisot et al. |
| 2001/0037100 A1 | 11/2001 | Shanklin |
| 2002/0119207 A1 | 8/2002 | Baker, Jr. et al. |
| 2002/0155084 A1 | 10/2002 | Roessler et al. |
| 2003/0194412 A1* | 10/2003 | Baker et al. ............... 424/192.1 |
| 2004/0043041 A1 | 3/2004 | Baker, Jr. et al. |
| 2005/0079185 A1 | 4/2005 | Parisot et al. |
| 2005/0208083 A1 | 9/2005 | Annis |
| 2005/0281843 A1 | 12/2005 | Singh |

FOREIGN PATENT DOCUMENTS

| | | |
|---|---|---|
| EP | 0549074 | 6/1993 |
| JP | 60-011429 | 1/1985 |
| JP | H05-294845 | 11/1993 |
| JP | H10-500686 | 1/1998 |
| WO | 94/00153 | 1/1994 |
| WO | 94/21292 | 9/1994 |
| WO | 95-11700 | 5/1995 |
| WO | 95/17210 | 6/1995 |
| WO | 97-29773 | 8/1997 |
| WO | 98/56414 | 12/1998 |
| WO | 99/11241 | 3/1999 |
| WO | 99/12565 | 3/1999 |
| WO | 99-33459 | 7/1999 |
| WO | 00-50006 | 8/2000 |
| WO | 00/62801 | 10/2000 |
| WO | 01/49296 | 7/2001 |
| WO | 2004-030608 | 4/2004 |
| WO | 2005-027872 | 3/2005 |

OTHER PUBLICATIONS

Klausner et al. The need for a global HIV vaccine enterprise. Science, vol. 300, Jun. 2003, pp. 2036-2039.*

(Continued)

*Primary Examiner* — Jeffrey Parkin
(74) *Attorney, Agent, or Firm* — Tyler J. Sisk; Casimir Jones, S.C.

(57) ABSTRACT

The present invention relates to methods and compositions for the stimulation of immune responses. Specifically, the present invention provides methods of inducing an immune response to human immunodeficiency virus (HIV) in a subject (e.g., a human subject) and compositions useful in such methods (e.g., a nanoemulsion comprising HIV or antigenic portion thereof).

**15 Cla

(56) References Cited

OTHER PUBLICATIONS

Figure 1A:
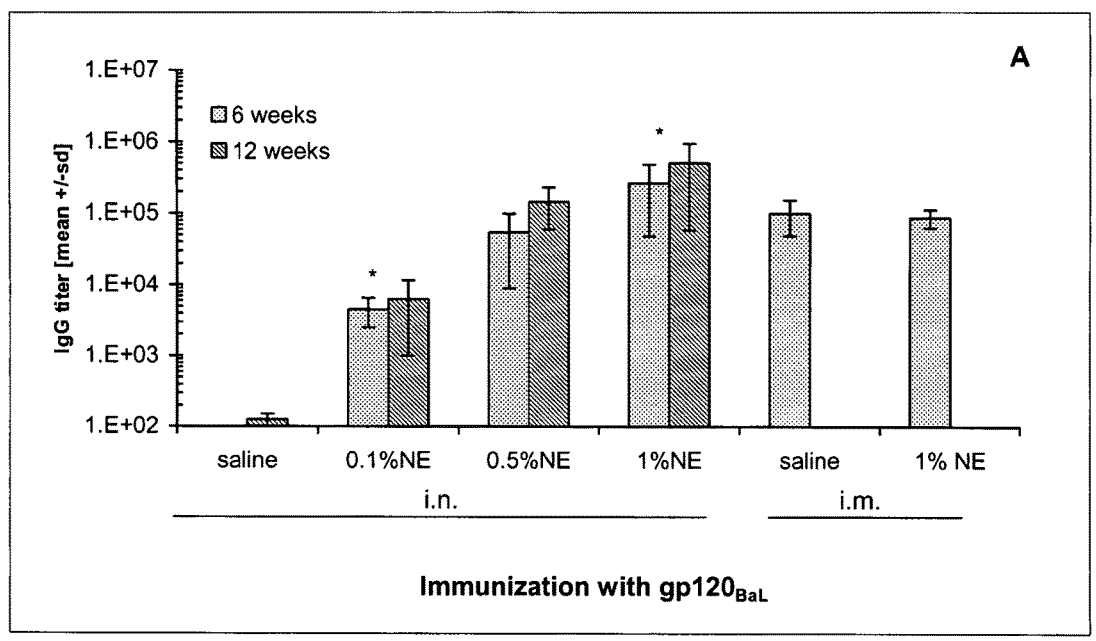

Desrosiers. Prospects for an AIDS vaccine. Nature Medicine, vol. 10(3), Mar. 2004, pp. 221-223.*
Nebel. Challenges and opportunities of development of an AIDS vaccine. Nature, vol. 410, Apr. 2001, pp. 1002-1007.*
Lee. Chapter 32 AIDS Vaccines: 32.1 Acquired immunodeficiency disease vaccines: design and development. AIDS: Biology, Diagnosis, Treatment, and Prevention, fourth edition, edited by DeVitat, Jr. et al., Lippincott-Raven, 1997, pp. 605-616.*
Bende. et al. Update: Search for an AIDS vaccine. AIDS Read, 10(9), 2000, pp. 526-537.*
Beyrer. The HIV/AIDS vaccine research effort: An update. The Johns Hopkins University AIDS Service, The Hopkins HIV Report, vol. 15 (1), Jan. 2003, pp. 1-16.*
Feinberg et al. AIDS vaccine models: challenging challenge viruses. Nature Medicine, vol. 8 (3), Mar. 2002, pp. 207-210.*
Burton, D. R., et al. 2004. HIV vaccine design and the neutralizing antibody problem. Nat. Immunol. 5(3):233-236.*
Gallo, R. C. 2005. The end or the beginning of the drive to an HIV-preventive vaccine: a view from over 20 years. The Lancet 366:1894-1898.*
Connick, E., et al. 2007. CTL fail to accumulate at sites of HIV-1 replication in lymphoid tissue. J. Immunol. 178:6975-6983.*
Walker, B. D., and D. R. Burton. 2008. Toward an AIDS vaccine. Science 320:760-764.*
Liao, H.-X., et al., May 2004, Immunogenicity of constrained monoclonal antibody A32-human immunodeficiency virus (HIV) Env gp120 complexes compared to that of recombinant HIV type 1 gp120 envelope glycoproteins, J. Virol. 78(10):5270-5278.*
Altemeier et al., Chloromycetin and Aureomycin in Experimental Gas Gangrene, Surgery, 28:621 (1950).
Baker Jr., et al., Enhanced systemic and mucosal immune responses in mice immunized with recombinant Bacillus anthracis protective antigen (rPA) using a novel nanoemulsion adjuvant, Journal of Allergy and Clinical Immunology, vol. 113, No. 2 Supplement, Feb. 2004, p. S292 XP 002560178 & 60th Annual Meeting of the American Academy of Allergy, Asthma and Immunology (AAAAI); San Francisco, CA, USA, Mar. 19-23, 2004.
Brown et al., Differential Diagnosis of Bacillus Cereus, Bacillus Anthracis, and Bacillus Cereus Var. Mycoides, J. Bact., 75:499 (1958).
Burdon and Wende, On the Differentiation of Anthrax Bacilli from Bacillus Cereus, J Infect. Diseas. 170(2):224-34 (1960).
Burdon et al., Experimental Infection of Mice with Bacillus Cereus: Studies of Pathogenesis and Pathologic Changes, J Infect. Diseas. 117:307 (1967).
Butterton et al., Development of a Germfree Mouse Model of Vibrio cholerae Infection, Infect. Immun., 64:4373 (1996).
Carter and Collins, The Route of Enteric Infection in Normal Mice, J. Exp. Med., 139:1189 (1974).
Castleman et al., Pathogenesis of Bronchiolitis and Pneumonia Induced in neonatal and Weanling Rats by Parainfluenza (Sendai) Virus, Am. J. Path., 129:277 (1987).
Castleman, Respiratory tract lesions in weanling outbred rats infected with Sendai virus, Am. J. Vet. Res., 44:1024 (1983).
Collins and Carter, Comparative Immunogenicity of Heat-Killed and Living Oral *Salmonella* Vaccines, Infect. Immun., 6:451 (1972).
Collins, Salmonellosis in Orally Infected Specific Pathogen-Free C557B1 Mice, Infect. Immun., 5:191 (1972).
Cox et al., Influenza virus: immunity and vaccination strategies, comparison of the immune response to inactivated and live, attenuated influenza vaccines. Scandinavian Journal of Immunology, vol. 59, p. 1-15, 2004.
Donovan et al., Prevention of murine influenza A virus pneumonitis by surfactant nano-emulsions. Antiviral Chemistry and Chemotherapy, 2000, vol. 11, pp. 41-49.
Drobniewski, Bacillus cereus and Related Species, Clin. Microbio. Rev. 6:324 (1993).

Eriksson et al., Virus validation of plasma-derived products produced by Pharmacia, with particular reference to immunoglobulins, Blood Coagulation and Fibtinolysis 5 (Suppl. 3):S37-S44 (1994).
Fields, Fields Virology, (Knipe, Howley (editors)), Lippincott Williams & Wilkins Publishers; Aug. 2001, p. 1555.
Finkelstein et al., Pathogenesis of Experimental Cholera in Infant Rabbits, J. Infect. Dis., 114:203 (1964).
Formal et al., Role of the Small intestine in an Experimental infection in Guinea Pigs, J. Bact. 85:119 (1963).
Freter, Experimental Enteric Shigella and Vibrio Infections in Mice and Guinea Pigs, J. Exp. Med., 104:411 (1956).
Freter, The Fatal Enteric Cholera Infection in the Guinea Pig, Achieved by Inhibition of Normal Enteric Flora, J. Infect. Dis., 97:57 (1955).
Fritz et al., Pathology of Experimental Inhalation Anthrax in the Rhesus Monkey, Lab. Invest. 73:691 (1995).
Halvorson and Church, Biochemistry of Spores of Aerobic Bacilli with Special Reference to Germination, Bacteriol Rev. 21:112 (1957).
Hamouda and Baker, Antimicrobial mechanism of action of surfactant lipid preparations in enteric Gram-negative bacilli, J. Appl. Microbiol., 89:397 (2000).
Hamouda et al., A Novel Surfactant nanoemulsion with Broad-Spectrum Sporicidal Activity against Bacillus Species, J. Infect Dis., 180:1939-1949 (1999).
Hills, Chemical Factors in the Germination of Spore-bearing Aerobes: observations on the Influence of Species, Strain and Conditions of Growth, J. Gen. Micro. 4:38 (1950).
Horowitz et al., Solvent/Detergent-Treated Plasma: A Virus-Inactivated Substitute for Fresh Frozen Plasma, Blood 79:826 (1992).
Jacoby et al., Sendai Viral Pneumonia in Aged BALB/c Mice, Exp. Gerontol., 29:89 (1994).
Johnson et al., Age-dependent Resistance to Viral Encephalitis: Studies of Infections Due to Sindbis Virus in Mice, J. Infect. Dis., 125:257 (1972).
Johnson et al., Virus Invasion of the Central Nervous System, Am. J. Path., 46:929 (1965).
Karaivanova and Spiro, Sulphation of N-linked oligosaccharides of vesicular stomatitis and influenza virus envelope blycoproteins: host cell specifity, subcellular localization and identification of substituted saccharides, Biochem J. 329(Pt 3):511 (1998).
Labrec et al., Epithelial Cell Penetration as an Essential Step in the Pathogenesis of Bacillary Dysentery, J. Bact. 88:1503 (1964).
Lamanna and Jones, Lethality for Mice of Vegetative and Spore Forms of Bacillus Cereus and Bacillus Cereus-Like Insect Pathogens Injected intraperitoneally and Subcutaneously, J. Bact. 85:532 (1963).
Levine et al., New Knowledge on Pathogenesis of Bacterial Enteric Infections as Applied to Vaccine Development, Microbiol. Rev., 47:510 (1983).
Maha and Igarashi, The Effect of Nonionic Detergent on Dengue and Japanese Encephalitis Virus Antigens in Antigen Detection Elisa and IgM-Capture Elisa, Southeast Asian J. Trop. Med. Pub. Health 28:718 (1997).
Mammen et al., Effective Inhibitors of Hemagglutination by Influenza Virus Synthesized from Plymers Having Active Ester Groups. insight into Mechanism of Inhibition, J Med Chem 38:4179 (1995).
Massion et al., Parainfluenza (Sendai) Virus Infects Ciliated Cells and Secretory Cells but Not Basal Cells of Rat Tracheal Epithelium, Am. J. Respir. Cell Mol. Biol. 9:361 (1993).
McMichael, Cytotoxic T Lymphocytes Specific for Influenza Virus, Curr. Top. Microbiol. Immunol. 189:75 (1994).
Mims and Murphy, Parainfluenza Virus Sendai Infection in Macrophages, Ependyma, Choroid Plexus, Vascular Endothelium and Respiratory Tract of Mice, Am. J. Path., 70:315 (1973).
Mor et al., Perspective: edible vaccines—a concept coming of age, Trends Micrbiol 6:449-53 (1998).
Naughton et al., A rat model of infection by *Salmonella typhimurium* or *Salm. enteritidis*, J. Appl. Bact., 81:651 (1996).
O'Hagan, D. Recent advances in Vaccine adjuvants for systemic and mucosal administration. J. Pharm. Pharmacol., 1997, vol. 49, 1-10.
Paul, Fundamental Immunology, Lippincott Williams & Wilkins Publishers; 5th edition Sep. 2003, p. 1353.

(56) References Cited

OTHER PUBLICATIONS

Perreault et al., Immunodominant minor histocompatibility antigens: the major ones, Immunol Today 19:69 (1998).
Portocala et al., Immunoelectrophoretic characterization of Sendai virus antigens, Virolegie 27:261 (1976).
Richter and Kipp, Transgenic Plants as Edible Vaccines, Curr Top Microbiol Immunol 240:159-76 (1999).
Roberts, Resistance of Vaccinia Virus to Inactivation by Solvent/Detergent Treatment of Blood Products, Biologicals (2000) 28, 29-32.
Ruedl and Wolf, Features of Oral Immunization, Int. Arch. Immunol., 108:334 (1995).
Russell, Bacterial Spores and Chemical Sporicidal Agents, Clin. Micro. 3:99 (1990).
Sandusky et al., An Evaluation of Aureomycin and Chloromycetin in Experimental Clostridium Welchii Infection, Surgery, 28:632 (1950).
Sercarz et al., Dominance and Crypticity of T Cell Antigenic Determinants, Anu Rev Immunol 11:729 (1993).
Silins et al., Development of Epstein-Barr Virus-specific Memory T Cell Receptor Clonotypes in Acute Infectious Mononucleosis, J Exp Med 184:1815 (1996).
Steven et al., Epitope Focusing in the Primary Cytotoxic T Cell Response to Epstein-Barr Virus and Its Relationship to T Cell memory, J Exp Med 184:1801 (1996).
Stevens et al., Comparison of Clindamycin, Rifampin, Tetracycline, metronidazole, and penicillin for Effiacy in Prevention of Experimental Gas Gangrene Due to clostridium perfringens, J. Infect. Dis., 155:220 (1987).
Stevens et al., Comparison of Single and Combination Antimicrobial Agents for Prevention of Experimental Gas Gangrene Caused by Clostridium perfringens, Antimicrob. Agents Chemother., 31:312 (1987).
Takeuchi et al., Experimental Bacillary Dysentery: An Electron Microscopic Study of the Response of the intestinal Mucosa to Bacterial Invasion, Am. J. Pathol., 47:1011 (1965).
Tremblay et al., T Lymphocyte Responses to Multiple Minor Histocompatibility Antigens Generate Both Self-Major Histocompatibility Complex-Restricted and Cross-Reactive Cytotoxic T Lymphocytes, Transplantation 58:59-67 (1994).
Tumpey et al., Mucosal delivery of inactivated influenza vaccine induces B-cell-dependent heterosubtypic cross-protection against lethal influenza a H5N1 virus infection. Journal of virology, Jun. 2001, vol. 75, No. 11, pp. 5141-5140.
Welkos and Friedlander, comparative safety and efficacy against Bacillus anthracis of protective antigen and live vaccines in mice, Microb Pathog 5:127 (1988).
Welkos et al., Differences in Susceptibility of Inbred Mice to Bacillus anthracis, Infect Immun. 51:795 (1986).
Yanagita, Biochemical Aspects on the Germination of Conidiospores of Aspergillus niger, Arch Mikrobiol 26:329 (1957).
JP Patent Application Kohyo Publication No. H06-507172 (unexamined Japanese national phase publication corresponding to a non-Japanese international publication).
JP Patent Application Kohyo Publication No. H05-508385 (unexamined Japanese national phase publication corresponding to a non-Japanese international publication).
Hamouda T et al: "A Novel Surfactant Nanoemulsion with a unique non-irritant topical antimicrobial activity against bacteria, enveloped viruses and fungi" Microbiological Research vol. 156, No. 1, Jan. 1, 2001, pp. 1-07.
Myc et al., Development of immune response that protects mice from viral pneumonitis after a single intranasal immunization with influenza A virus and nanoemulsion, Vaccine, Sep. 2003, vol. 21 (25-26), pp. 3801-3814.
Turner et al., Inactivated smallpox vaccine. A comparison of inactivation methods; J. Hyg., Camb., 1970, 68, p. 197.
Chen, H., Recent advances in mucosal vaccine development, J Control Release. Jul. 3, 2000;67(2-3):117-28.
Debin, A., et al., Intranasal immunization with recombinant antigens associated with new cationic particles induces strong mucosal as well as systemic antibody and CTL responses, Vaccine. Jun. 21, 2002;20(21-22):2752-63.
Doyle et al., IRF3 mediates a TLR3/TLR4-specific antiviral gene program, Immunity. Sep. 2002;17(3):251-63.
Neutra, M.R. and P.A. Kozlowski, Mucosal vaccines: the promise and the challenge, Nat Rev Immunol. Feb. 2006;6 (2):148-58.
Pittman, Aluminum-containing vaccine associated adverse events: role of route of administration and gender, Vaccine. May 31, 2002;20 Suppl 3:S48-50.
Murphey-Corb et al., A Formalin-Inactivated Whole SIV Vaccine Confers Protection in Macaques, Science, New Series, vol. 246, No. 4935 (Dec. 8, 1989), pp. 1293-1297.
Lin et al., Acute inhalation toxicity of cetylpyridinium chloride, Food Chem Toxicol. Dec. 1991;29(12):851-4.
Paley, O. (2014). Cetylpyridinium Chloride. Synlett, 25(04), 599-600.

* cited by examiner

METHODS OF INDUCING HUMAN IMMUNODEFICIENCY VIRUS-SPECIFIC IMMUNE RESPONSES IN A HOST COMPRISING NASALLY ADMINISTERING COMPOSITIONS COMPRISING A NAONEMULSION AND RECOMBINANT GP120 IMMUNOGEN

The present invention claims priority to U.S. Provisional Patent Application Ser. No. 60/791,758 filed Apr. 13, 2006, hereby incorporated by reference in its entirety.

This invention was made with government support under contract U54 AI57153-02 awarded by the National Institutes of Health and contract MDA972-97-1-0007 awarded by the Department of Defense-Defense Advanced Research Projects Agency. The government has certain rights in the invention.

FIELD OF THE INVENTION

The present invention relates to methods and compositions for the stimulation of immune responses. Specifically, the present invention provides methods of inducing an immune response to human immunodeficiency virus (HIV) in a subject (e.g., a human subject) and compositions useful in such methods (e.g., a nanoemulsion comprising HIV or antigenic portion thereof).

BACKGROUND OF THE INVENTION

Human immunodeficiency virus-1 (HIV-1) is the primary cause of the acquired immune deficiency syndrome (AIDS) which is regarded as one of the world's major health problems. Although extensive research throughout the world has been conducted to produce a vaccine, such efforts thus far have not been successful.

The major goal, not previously attained, has been the generation of an immune response in a subject characterized by antibody titer generation that neutralize virus in vitro at titers reaching both the level and complexity (e.g., ability to neutralize more than one isolate) seen in human sera from infected individuals. Neutralizing antibodies in humans have mapped to the envelope protein, gp160, or one of its component parts (gp120 or gp41), and thus most vaccine efforts have concentrated on the development of envelope-protein-related antigens.

Thus, there remains a need for immunogenic substances capable of inducing an immune response in a subject (e.g., characterized by neutralizing antibodies against HIV), preferably using a single source material that induces neutralizing antibodies against a variety of field isolates of HIV. Furthermore, substances capable of inducing both systemic as well as mucosal immunity to HIV would be highly desirable, as one of the surfaces most commonly exposed to HIV in humans is vaginal mucosa.

SUMMARY OF THE INVENTION

The present invention relates to methods and compositions for the stimulation of immune responses. Specifically, the present invention provides methods of inducing an immune response to human immunodeficiency virus (HIV) in a subject (e.g., a human subject) and compositions useful in such methods (e.g., a nanoemulsion comprising HIV or antigenic portion thereof).

Accordingly, in some embodiments, the present invention provides a method of inducing an immune response to HIV in a subject comprising providing a composition comprising a nanoemulsion and an immunogen, wherein the immunogen comprises recombinant gp120; and administering the composition to the subject under conditions such that the subject generates an immune response to the HIV. The present invention is not limited by the type of immunogen utilized (e.g., recombinant gp120). For example, in some embodiments, the immunogen is an isolated, purified or recombinant Tat, Nef or other immunogenic HIV protein, or derivative thereof. In some embodiments, the immunogen comprises HIV inactivated by the nanoemulsion. The present invention is not limited by the nature of the immune response generated. Indeed, a variety of immune responses may be generated and measured in a subject administered a composition comprising a nanoemulsion and an immunogen of the present invention including, but not limited to, activation, proliferation or differentiation of cells of the immune system (e.g., B cells, T cells, dendritic cells, antigen presenting cells (APCs), macrophages, natural killer (NK) cells, etc.); up-regulated or down-regulated expression of markers and cytokines; stimulation of IgA, IgM, or IgG titer; splenomegaly (e.g., increased spleen cellularity); hyperplasia, mixed cellular infiltrates in various organs, and other responses (e.g., of cells) of the immune system that can be assessed with respect to immune stimulation known in the art. In some embodiments, administering comprises contacting a mucosal surface of the subject with the composition. The present invention is not limited by the mucosal surface contacted. In some preferred embodiments, the mucosal surface comprises nasal mucosa. In some embodiments, the mucosal surface comprises vaginal mucosa. In some embodiments, administrating comprises parenteral administration. The present invention is not limited by the route chosen for administration of a composition of the present invention. In some embodiments, inducing an immune response induces immunity to said HIV in said subject. In some embodiments, the immunity comprises systemic immunity. In some embodiments, the immunity comprises mucosal immunity. In some embodiments, the immune response comprises increased expression of IFN-γ in the subject. In some embodiments, the immune response comprises a systemic IgG response. In some embodiments, the immune response comprises a mucosal IgA response. In some embodiments, the composition comprises between 15 and 75 μg of recombinant gp120. However, the present invention is not limited to this amount of recombinant gp120 administered. For example, in some embodiments, more than 75 μg of recombinant gp120 is present in a dose administered to the subject. In some embodiments, less than 15 μg of recombinant gp120 is present in a dose administered to a subject. In some embodiments, the composition comprises a 10% nanoemulsion solution. However, the present invention is not limited to this amount (e.g., percentage) of nanoemulsion. For example, in some embodiments, a composition comprises less than 10% nanoemulsion. In some embodiments, a composition comprises more than 10% nanoemulsion. In some embodiments, the nanoemulsion comprises $W_{20}5EC$. The present invention is not limited by the type of nanoemulsion utilized. Indeed, a variety of nanoemulsions are contemplated to be useful in the present invention. For example, in some preferred embodiments, the nanoemulsion (e.g., for generating an immune response (e.g., for use as a vaccine)) comprises an oil-in-water emulsion, the oil-in-water emulsion comprising a discontinuous oil phase distributed in an aqueous phase, a first component comprising a solvent (e.g., an alcohol or glycerol), and a second component comprising a surfactant or a halogen-containing compound. The aqueous phase can comprise any type of aqueous phase including, but not limited to, water (e.g., $diH_2O$, distilled water, tap water) and solutions (e.g., phosphate buffered saline solution). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In some preferred embodiments, the oil phase comprises 30-90 vol % of the oil-in-water emulsion (i.e., constitutes 30-90% of the total volume of the final emulsion), more preferably 50-80%. While the present invention in not limited by the nature of the alcohol component, in some preferred embodiments, the alcohol is ethanol or methanol. Furthermore, while the present invention is not limited by the nature of the surfactant, in some preferred embodiments, the surfactant is a polysorbate surfactant (e.g., TWEEN 20, TWEEN 40, TWEEN 60, and TWEEN 80), a pheoxypolyethoxyethanol (e.g., TRITON X-100, X-301, X-165, X-102, and X-200, and TYLOX-APOL) or sodium dodecyl sulfate. Likewise, while the present invention is not limited by the nature of the halogen-containing compound, in some preferred embodiments, the halogen-containing compound comprises a cetylpyridinium halides, cetyltrimethylammonium halides, cetyldimethylethylammonium halides, cetyldimethylbenzylammonium halides, cetyltributylphosphonium halides, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyidimethylethylammonium bromide, cetyltributylphosphonium bromide, dodecyltrimethylammonium bromide, or tetrad ecyltrimethylammonium bromide. Nanoemulsions of the present invention may further comprise third, fourth, fifth, etc. components. In some preferred embodiments, an additional component is a surfactant (e.g., a second surfactant), a germination enhancer, a phosphate based solvent (e.g., tributyl phosphate), a neutramingen, L-alanine, ammonium chloride, trypticase soy broth, yeast extract, L-ascorbic acid, lecithin, p-hyroxybenzoic acid methyl ester, sodium thiosulate, sodium citrate, inosine, sodium hyroxide, dextrose, and polyethylene glycol (e.g., PEG 200, PEG 2000, etc.). In some embodiments, the oil-in-water emulsion comprises a quaternary ammonium compound. In some preferred embodiments, the oil-in-water emulsion has no detectable toxicity to plants or animals (e.g., to humans). In other preferred embodiments, the oil-in-water emulsion causes no detectable irritation to plants or animals (e.g., to humans). In some embodiments, the oil-in-water emulsion further comprises any of the components described above. Quaternary ammonium compounds include, but are not limited to, N-alkyldimethyl benzyl ammonium saccharinate, 1,3,5-Triazine-1,3,5(2H, 4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy) ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis(alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride. In some embodiments, the emulsion lacks any antimicrobial substances (i.e., the only antimicrobial composition is the emulsion itself). In some embodiments, the nanoemulsion is X8P. In some embodiments, immunity protects the subject from displaying signs or symptoms of disease caused by HIV. In some embodiments, immunity protects the subject from challenge with a subsequent exposure to live HIV. In some embodiments, the composition further comprises an adjuvant. The present invention is not limited by the type of adjuvant utilized. In some embodiments, the adjuvant is a CpG oligonucleotide. In some embodiments, the adjuvant is monophosphoryl lipid A. A number of other adjuvants that find use in the present invention are described herein. In some embodiments, the subject is a human. In some embodiments, the immunity protects the subject from displaying signs or symptoms of AIDS. In some embodiments, immunity reduces the risk of infection upon one or more exposures to HIV.

The present invention also provides a composition for stimulating an immune response comprising a nanoemulsion and an HIV immunogen (e.g., recombinant gp120), wherein the composition is configured to induce immunity to HIV in a subject. In some embodiments, the nanoemulsion comprises any nanoemulsion described herein. In some embodiments, the nanoemulsion comprises $W_{20}5EC$. In some embodiments, the nanoemulsion comprises X8P. In some embodiments, the composition provides a subject between 15 and 75 µg of recombinant gp120 when administered to the subject. In some embodiments, a dose of the composition administered to a subject comprises between a 0.1% and 20% nanoemulsion solution. In some embodiments, a dose of the composition administered to a subject comprises a 1% nanoemulsion solution. In some embodiments, recombinant gp120 is heat stable in the nanoemulsion. In some embodiments, the composition is diluted prior to administration to a subject. In some embodiments, the subject is a human. In some embodiments, immunity is systemic immunity. In some embodiments, immunity is mucosal immunity. In some embodiments, the composition further comprises an adjuvant. In some embodiments, the adjuvant comprises a CpG oligonucleotide. In some embodiments, the adjuvant comprises monophosphoryl lipid A.

The present invention also provides a kit comprising a composition for stimulating an immune response comprising a nanoemulsion and an HIV immunogen (e.g., recombinant gp120), wherein the composition is configured to induce immunity to HIV in a subject, and instructions for administering the composition. In some embodiments, the kit comprises a nanoemulsion in contact with an object (e.g., an applicator). In some embodiments, the kit comprises a device for administering the composition. The present invention is not limited by the type of device included in the kit for administering the composition. Indeed, many different devices may be included in the kit including, but not limited to, a nasal applicator, a syringe, a nasal inhaler and a nasal mister. In some embodiments, the kit comprises a vaginal applicator, vaginal mister or other type of device for vaginal administration (e.g., to the vaginal mucosa) of a composition of the present invention. In some embodiments, a kit comprises a birth control device (e.g., a condom, an IUD, sponge, etc.) coated with a nanoemulsion composition of the present invention. In some embodiments, a nanoemulsion composition of the present invention is mixed in a douche or a suppository or a lubricant (e.g., sexual lubricant). In some embodiments, the present invention provides systems and methods (e.g., using a nanoemulsion composition of the present invention) for large scale administration (e.g., to a population of a city, village, town, state or country). In preferred embodiments, such large scale administrations are carried out in a manner that is easy to use (e.g., nasal administration) and that is culturally sensitive (e.g., so as not to offend those being administered a composition of the present invention).

DESCRIPTION OF THE DRAWINGS

FIG. 1 shows antibody response in mice intranasally vaccinated with two serotypes of recombinant gp120 and nanoemulsion adjuvant. (A) Induction of serum anti-$gp120_{BaL}$ IgG in mice immunized with $gp120_{BaL}$ mixed with 0.1%, 0.5% and 1% NE. Anti-$gp120_{BaL}$ IgG antibodies were measured at 6 weeks (after two doses) and 12 weeks (after three doses). Intranasal (i.n.) and intramuscular (i.m.) routes of immunization are indicated in the Figure. (B) Induction of anti-$gp120_{SF162}$ IgG in mice i.n. immunized with two doses of $gp120_{SF162}$ in 1% NE alone or with addition of CpG or MPL A. Anti-gp120 IgG antibodies were measured at 6 weeks. Anti gp120 antibody levels are presented as a mean of endpoint titers (+/−s.d.) in serum of individual animals. Cross-reactivity of the anti-gp120 antibodies. Serum IgG from mice immunized with either (C) $gp120_{BaL}$ or (D) $gp120_{SF162}$ reacts both with an autologous and with heterologous serotypes of antigen. Data presented as titration curves of pooled anti-gp120 sera on plates coated with either $gp120_{SF162}$ or $120_{BaL}$ serotypes of antigen.

FIG. 2 shows nasal immunization with gp120/NE induces mucosal IgA. Significant levels of secretory anti-gp120 IgA and IgB antibodies (A and B, respectively) were present in bronchial lavage (BAL), and anti-gp120 IgA antibodies were present in serum and in the vaginal washes (C) of mice vaccinated with $gp120_{BaL}$ and NE adjuvant. Anti-gp120 IgA concentration is presented as mean absorbance (OD 405 nm +/−s.d.) obtained in ELISA performed with 1:2 diluted BAL fluids (A and B), undiluted vaginal washes (C), and 1:50 diluted serum (C). Statistically significant differences were observed between gp120/saline and each gp120/NE groups ($p<0.05$).

FIG. 3 shows (A) Antigen-specific splenocyte proliferation. Splenocytes from immunized animals were stimulated in vitro with 2 μg/ml of autologous recombinant $gp120_{BaL}$. Cell proliferation was normalized to controls and presented as mean+/−s.d. of individual proliferation indexes. The differences between the $gp120_{BaL}$/saline and the $gp120_{BaL}$/NE groups were statistically significant ($p<0.05$). (B) Antigen-specific activation of cytokine production in splenocytes in vitro. Splenocytes from immunized mice were activated with 2 μg/ml of autologous and heterologous serotypes of gp120 (BaL and SF162, respectively) and with 20 μM of the V3 loop peptide. The released IFN-γ was determined by ELISA and concentration is presented as a mean of individual samples+/−s.d.

FIG. 4 shows (A) Nasal immunization of guinea pig. Hartly guinea pigs (GP) were vaccinated in the prime-boost schedule with 50 μg $gp120_{SF162}$ in 1% NE. The serum IgG antibody response toward $gp120_{SF162}$ and $_{BaL}$ serotypes was measured at six weeks. Anti-gp120 IgG are presented as absorption values (OD 405 nm, +/−s.d.) obtained in ELISA with 1:200 dilution of serum using plates coated with $gp120_{SF162}$gp (autologous) and $120_{BaL}$ (heterologous) serotypes of antigen. (B) Neutralizing antibody produced by i.n. immunization with $gp120_{SF162}$/NE. The neutralization of laboratory strains and primary isolates of HIV were performed in the TZM-BL cell system. $NT_{50}$ values represent the serum dilution at which relative luminescence units (RLU) were reduced 50% compared to virus control. Individual preimmune sera were used to evaluate nonspecific antiviral activity.

DEFINITIONS

To facilitate an understanding of the present invention, a number of terms and phrases are defined below:

As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

The terms "host" or "subject," as used herein, refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention (e.g., a composition for inducing an immune response).

As used herein, the terms "inactivating," "inactivation" and grammatical equivalents, when used in reference to a microorganism (e.g., a pathogen (e.g., a virus (e.g., human immunodeficiency virus (HIV)))), refer to the killing, elimination, neutralization and/or reducing of the capacity of the mircroorganism (e.g., a pathogen (e.g., a virus (e.g., HIV))) to infect and/or cause a pathological response and/or disease in a host. In some preferred embodiments, the present invention provides a composition comprising nanoemulsion (NE)-inactivated HIV. Accordingly, as referred to herein, compositions comprising "NE-inactivated HIV," "NE-killed HIV," NE-neutralized HIV" or grammatical equivalents refer to compositions that, when administered to a subject, are characterized by the absence of, or significantly reduced presence of, HIV replication (e.g., over a period of time (e.g., over a period of days, weeks, months, or longer)) within the host.

As used herein, the term "fusigenic" is intended to refer to an emulsion that is capable of fusing with the membrane of a microbial agent (e.g., a bacterium or bacterial spore). Specific examples of fusigenic emulsions are described herein.

As used herein, the term "lysogenic" refers to an emulsion (e.g., a nanoemulsion) that is capable of disrupting the membrane of a microbial agent (e.g., a virus (e.g., viral envelope) or a bacterium or bacterial spore). In preferred embodiments of the present invention, the presence of a lysogenic and a fusigenic agent in the same composition produces an enhanced inactivating effect compared to either agent alone. Methods and compositions (e.g., for inducing an immune response (e.g., used as a vaccine) using this improved antimicrobial composition are described in detail herein.

The term "emulsion," as used herein, includes classic oil-in-water or water in oil dispersions or droplets, as well as other lipid structures that can form as a result of hydrophobic forces that drive apolar residues (e.g., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in preferred embodiments, the nanoemulsions comprise an oil phase having droplets with a mean particle size of approximately 0.1 to 5 microns (e.g., 150+/−25 nm in diameter), although smaller and larger particle sizes are contemplated. The terms "emulsion" and "nanoemulsion" are often used herein, interchangeably, to refer to the nanoemulsions of the present invention.

As used herein, the terms "contact," "contacted," "expose," and "exposed," when used in reference to a nanoemulsion and a live microorganism, refer to bringing one or more nanoemulsions into contact with a microorganism (e.g., a pathogen) such that the nanoemulsion inactivates the microorganism or pathogenic agent, if present. The present invention is not limited by the amount or type of nanoemulsion used for microorganism inactivation. A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion (e.g., sufficient for inactivating the microorganism (e.g., virus inactivation)) and microorganisms (e.g., sufficient to provide an antigenic composition (e.g., a composition capable of inducing an immune response)) are contemplated in the present invention including, but not limited to, those described herein (e.g., in Example 1).

The term "surfactant" refers to any molecule having both a polar head group, which energetically prefers solvation by water, and a hydrophobic tail that is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described, for example, by Meyers, (See, e.g., Meyers, *Surfactant Science and Technology*, VCH Publishers Inc., New York, pp. 231-245 (1992)), incorporated herein by reference. As used herein where appropriate, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein the term "interaction enhancers" refers to compounds that act to enhance the interaction of an emulsion with a microorganism (e.g., with a cell wall of a bacteria (e.g., a Gram negative bacteria) or with a viral envelope (e.g., Vaccinia virus envelope)). Contemplated interaction enhancers include, but are not limited to, chelating agents (e.g., ethylenediaminetetraacetic acid (EDTA), ethylenebis (oxyethylenenitrilo)tetraacetic acid (EGTA), and the like) and certain biological agents (e.g., bovine serum abulmin (BSA) and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., resulting in total or partial immunity to a microorganism (e.g., pathogen) capable of causing disease). In preferred embodiments of the invention, the composition comprises a nanoemulsion and an immunogen (e.g., wherein the immunogen comprises HIV or an immunogenic protein or epitope thereof (e.g., gp120). In further preferred embodiments, the composition comprising a nanoemulsion and an immunogen comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response (e.g. that decreases the infectivity, morbidity, or onset of mortality in a subject (e.g., caused by exposure to a pathogenic microorganism) or that prevents infectivity, morbidity, or onset of mortality in a subject (e.g., caused by exposure to a pathogenic microorganism)). Thus, in some preferred embodiments, a composition comprising a nanoemulsion and an immunogen (e.g., HIV or an immunogenic protein or epitope thereof (e.g., gp120)) is administered to a subject as a vaccine (e.g., to prevent or attenuate a disease (e.g., by providing to the subject total or partial immunity against the disease or the total or partial attenuation (e.g., suppression) of a sign, symptom or condition of the disease (e.g., AIDS).

As used herein, the term "adjuvant" refers to any substance that can stimulate an immune response (e.g., a mucosal immune response). Some adjuvants can cause activation of a cell of the immune system (e.g., an adjuvant can cause an immune cell to produce and secrete a cytokine). Examples of adjuvants that can cause activation of a cell of the immune system include, but are not limited to, saponins purified from the bark of the *Q. saponaria* tree, such as QS21 (a glycolipid that elutes in the 21.sup.st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). Traditional adjuvants are well known in the art and include, for example, aluminum phosphate or hydroxide salts ("alum"). In some embodiments, compositions of the present invention (e.g., comprising HIV or an immunogenic epitope thereof (e.g., gp120)) are administered with one or more adjuvants (e.g., to skew the immune response towards a Th1 or Th2 type response).

As used herein, the term "an amount effective to induce an immune response" (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route.

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide))

to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) or portion thereof (e.g., a protein antigen (e.g., gp120 or rPA))) that is capable of eliciting an immune response in a subject. In preferred embodiments, immunogens elicit immunity against the immunogen (e.g., microorganism (e.g., pathogen or a pathogen product)) when administered in combination with a nanoemulsion of the present invention.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention (e.g., a composition for inducing an immune response (e.g., a composition comprising a nanoemulsion and an immunogen)) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, etc.), topically, and the like.

As used herein, the terms "co-administration" and "co-administering" refer to the administration of at least two agent(s) (e.g., a composition comprising a nanoemulsion and an immunogen and one or more other agents—e.g., an adjuvant) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent. In other embodiments, co-administration is preferable to elicit an immune response in a subject to two or more different immunogens (e.g., microorganisms (e.g., pathogens)) at or near the same time (e.g., when a subject is unlikely to be available for subsequent administration of a second, third, or more composition for inducing an immune response).

As used herein, the term "topically" refers to application of a compositions of the present invention (e.g., a composition comprising a nanoemulsion and an immunogen) to the surface of the skin and/or mucosal cells and tissues (e.g., alveolar, buccal, lingual, masticatory, vaginal or nasal mucosa, and other tissues and cells which line hollow organs or body cavities).

In some embodiments, the compositions of the present invention are administered in the form of topical emulsions, injectable compositions, ingestible solutions, and the like. When the route is topical, the form may be, for example, a spray (e.g., a nasal spray), a cream, or other viscous solution (e.g., a composition comprising a nanoemulsion and an immunogen in polyethylene glycol).

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethylethe glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease.

"Nasal application", as used herein, means applied through the nose into the nasal or sinus passages or both. The application may, for example, be done by drops, sprays, mists, coatings or mixtures thereof applied to the nasal and sinus passages.

"Vaginal application", as used herein, means applied into or through the vagina so as to contact vaginal mucosa. The application may contact the urethra, cervix, fornix, uterus or other area surrounding the vagina. The application may, for example, be done by drops, sprays, mists, coatings, lubricants or mixtures thereof applied to the vagina or surrounding tissue.

As used herein, the term "kit" refers to any delivery system for delivering materials. In the context of immunogenic agents (e.g., compositions comprising a nanoemulsion and an immunogen), such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunogenic agents (e.g., nanoemulsions) and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a nanoemulsion and an immunogen for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

As used herein, the term "HIV immunogen" refers to a protein or peptide antigen derived from HIV that is capable of generating an immune response in a subject. Examples of HIV immunogens include, but are not limited to, gp160, gp120, gp41, Tat, and Nef proteins, and antigenic portions thereof. An immunogen may be an isolated wild type or mutant protein, or a recombinant or synthesized protein or peptide antigen or a derivative or variant thereof.

DETAILED DESCRIPTION OF THE INVENTION

The present invention relates to methods and compositions for the stimulation of immune responses. Specifically, the present invention provides methods of inducing an immune response to human immunodeficiency virus (HIV) in a subject (e.g., a human subject) and compositions useful in such methods (e.g., a nanoemulsion comprising HIV or antigenic portion thereof).

The HIV envelope glycoprotein gp120 is the viral protein that is used for attachment to the host cell. This attachment is mediated by the binding to two surface molecules of helper T cells and macrophages, known as CD4 and one of the two chemokine receptors CCR-4 or CXCR-5. The gp120 protein is first expressed as a larger precursor molecule (gp 160), which is then cleaved post-translationally to yield gp120 and gp41. The gp120 protein is retained on the surface of the virion by linkage to the gp41 molecule, which is inserted into the viral membrane.

The gp120 protein is the principal target of neutralizing antibodies. The most immunogenic regions of the gp120 proteins (V3 loop) are also the most variable parts of the protein. The gp120 protein also contains epitopes that are recognized by cytotoxic T lymphocytes (CTL). These effector cells are able to eliminate virus-infected cells, and therefore constitute a second major antiviral immune mechanism. In contrast to the target regions of neutralizing antibodies some CTL epitopes appear to be relatively conserved among different HIV strains. For this reason gp120 and gp 160 are considered to be useful antigenic components in vaccines that aim at eliciting cell-mediated immune responses (particularly CTL).

Several types of gp120 immunogenic antigens have been developed: (1) purified gp120 derived from HIV-infected tissue culture cells (referred to herein as "viral-derived gp120"); (2) gp120 made in cells infected with recombinant viruses, such as vaccinia or baculovirus (referred to herein as "live-virus-vector-derived gp120 and gp160"); (3) recombinant gp120 made in mammalian cells (referred to herein as "recombinant mammalian gp120"); (4) recombinant denatured polypeptides that represent all or various portions of gp120 and gp41 (referred to herein as "recombinant denatured antigens"); and (5) peptides that represent small segments of gp120 and gp41 (referred to herein as "peptides").

In general, each of these immunogenic antigens are highly immunogenic as adjuvanted in a variety of species. They have generated antibodies capable of neutralizing the homologous isolate of HIV-1. Levels of neutralization have not (in general) reached the level of neutralizing titer found in infected humans and there has been much difficulty generating an immunogenic composition that generates immunity to more than one strain of HIV (e.g., other than the strain from which the immunogenic antigen was derived).

Another factor that has been particularly difficult to overcome when preparing HIV-1 vaccines is sequence diversity. HIV-1 and HIV-2 are characterized by having a very high level of sequence diversity that is most pronounced in the gp120 portion of the envelope. This sequence diversity is clustered in regions known as hypervariable regions. Many have proposed using a vaccine cocktail, comprising antigenic substances derived from a variety of HIV isolates, to provide protection against a broad range infective sources. The present invention is well suited for delivery of a composition comprising a variety of HIV antigenic substances derived from a variety of HIV isolates (See Examples 1 and 6).

Thus, there remains a need for immunogenic substances capable of inducing neutralizing antibodies against HIV, preferably using a single source material that induces neutralizing antibodies against a variety of field isolates of HIV. Furthermore, substances capable of inducing both systemic as well as mucosal immunity to HIV would be highly desirable, as one of the surfaces most commonly exposed to HIV in humans is vaginal mucosa.

Accordingly, the present invention provides methods of inducing an immune response to HIV in a subject (e.g., a human subject) and compositions useful in such methods (e.g., a nanoemulsion comprising HIV or HIV components (e.g., isolated or recombinant HIV proteins). In some embodiments, methods of inducing an immune response provided by the present invention are used for vaccination. Due to the rate of adverse events with existing HIV vaccines, the present invention provides a significant improvement in HIV vaccination safety without compromising vaccine efficacy.

For example, the present invention describes the development of immunity (e.g., HIV immunity) in a subject after mucosal administration (e.g., mucosal vaccination) with a composition comprising a nanoemulsion and an immunogenic protein from HIV (e.g., recombinant gp120) generated and characterized during development of the present invention (See Examples 1-6). Nanoemulsion (NE), a surface-active antimicrobial material, was mixed with recombinant gp120 from either BaL or SF162 serotypes, resulting in an immunogenic composition comprising NE and recombinant gp120 that is stable at room temperature (e.g., in some embodiments, for more than 2 weeks, more preferably more than 3 weeks, even more preferably more than 4 weeks, and most preferably for more than 5 weeks) and that can be used to induce an immune response against HIV in a subject (e.g., that can be used either alone or as an adjuvant for inducing an anti-HIV immune response).

Mucosal administration of a composition comprising NE and an HIV immunogen (e.g., recombinant gp120) to a subject resulted in high-titer mucosal and systemic antibody responses and generated a Th1 type cellular immune response (See, e.g., Examples 1, 2, and 5). Further, antibodies generated against one serotype of gp120 cross-reacted with other gp120 serotypes (See, e.g., Example 3). Moreover, mice immunized intranasally with a composition comprising NE and recombinant gp120 generated mucosally secreted, anti-gp120 specific IgA antibodies that were detectable in both bronchial as well as vaginal mucosal surfaces (See Example 4). Thus, mice administered a composition of the present invention generated a mucosal immune response to HIV. The immune response generated in mice administered a composition comprising a NE and recombinant gp120 was also capable of neutralizing HIV (See Example 6).

Thus, in some embodiments, the present invention provides that administration (e.g., mucosal administration) of a composition comprising NE and an HIV immunogen (e.g., recombinant gp120) is sufficient to induce a protective immune response against HIV in a subject (e.g., protective immunity (e.g., mucosal and systemic immunity)). In some embodiments, a subsequent administration (e.g., one or more boost administrations subsequent to a primary administration) to a subject provides the induction of an enhanced immune response to HIV in the subject. Thus, the present invention demonstrates that administration of a composition comprising NE and an HIV immunogen (e.g., recombinant gp120) to a subject provides protective immunity against AIDS.

Although an understanding of the mechanism is not necessary to practice the present invention and the present invention is not limited to any particular mechanism of action, in some embodiments, combining a NE and an HIV immunogen (e.g., recombinant gp120) from one or more serotypes of HIV stabilizes the HIV immunogen (e.g., recombinant gp120) and provides the proper substance for generation of an immune response. In other embodiments, because NE formulations can penetrate the mucosa through pores, they may carry immunogenic proteins to the submucosal location of dendritic cells (e.g., thereby initiating and/or stimulating an immune response).

Although an understanding of the mechanism is not necessary to practice the present invention and the present invention is not limited to any particular mechanism of action, in some embodiments, NE treatment (e.g., neutralization of HIV with a NE of the present invention) preserves important viral neutralizing epitopes (e.g., recognizable by a subject's immune system), stabilizing their hydrophobic and hydrophilic components in the oil and water interface of the emulsion (e.g., thereby providing one or more immunogens (e.g., stabilized antigens) against which a subject can mount an immune response). In other embodiments, because NE formulations are known to penetrate the mucosa through pores, they may carry viral proteins to the submucosal location of dendritic cells (e.g., thereby initiating and/or stimulating an immune response).

Dendritic cells avidly phagocytose NE oil droplets and this could provide a means to internalize immunogenic proteins for antigen presentation. While other vaccines rely on inflammatory toxins or other immune stimuli for adjuvant activity (See, e.g., Holmgren and Czerkinsky, Nature Med. 2005, 11; 45-53), NEs have not been shown to be inflammatory when placed on the skin or mucous membranes in studies on animals and in humans. Thus, although an understanding of the mechanism is not necessary to practice the present invention and the present invention is not limited to any particular mechanism of action, in some embodiments, a composition comprising a NE of the present invention (e.g., a composition comprising NE and recombinant HIV proteins (e.g., gp120) from one or more serotypes of HIV may act as a "physical" adjuvant (e.g., that transports and/or presents HIV proteins (e.g., gp120) to the immune system. In some preferred embodiments, mucosal administration of a composition of the present invention generates mucosal as well as systemic immunity (e.g., signs of mucosal immunity (e.g., generation of IgA antibody titers).

Both cellular and humoral immunity play a role in protection against HIV and both were induced with the NE formulations (See, e.g., Examples 2-6). Thus, in some embodiments, administration (e.g., mucosal administration) of a composition of the present invention to a subject results in the induction of both humoral (e.g., development of specific antibodies) and cellular (e.g., cytotoxic T lymphocyte) immune responses (e.g., against HIV proteins (gp120)). In some preferred embodiments, a composition of the present invention (e.g., a composition comprising a NE and recombinant gp120 from one or more serotypes of HIV) is used as a AIDS vaccine.

Furthermore, in preferred embodiments, a composition of the present invention induces (e.g., when administered to a subject) both systemic and mucosal immunity. Thus, in some preferred embodiments, administration of a composition of the present invention to a subject results in protection against an exposure (e.g., a mucosal exposure) to HIV. Although an understanding of the mechanism is not necessary to practice the present invention and the present invention is not limited to any particular mechanism of action, mucosal administration (e.g., vaccination) provides protection against HIV infection (e.g., that initiates at a mucosal surface). Although it has heretofore proven difficult to stimulate secretory IgA responses and protection against pathogens that invade at mucosal surfaces (See, e.g., Mestecky et al, Mucosal Immunology. 3ed edn. (Academic Press, San Diego, 2005)), the present invention provides compositions and methods for stimulating mucosal immunity (e.g., a protective IgA response) from a pathogen in a subject.

In some embodiments, the present invention provides a composition (e.g., a composition comprising a NE and immunogenic protein antigens from HIV (e.g., gp120) to serve as a mucosal vaccine. This material can easily be produced with NE and HIV protein (e.g., viral-derived gp120, live-virus-vector-derived gp120 and gp160, recombinant mammalian gp120, recombinant denatured antigens, small peptide segments of gp120 and gp41, V3 loop peptides (See, e.g., Example 1)), and induces both mucosal and systemic immunity (See, e.g., Examples 2-6). The ability to produce this formulation rapidly and administer it via mucosal (e.g., nasal or vaginal) instillation provides a vaccine that can be used in large-scale administrations (e.g., to a population of a town, village, city, state or country).

In some preferred embodiments, the present invention provides a composition for generating an immune response comprising a NE and an immunogen (e.g., a purified, isolated or synthetic HIV protein or derivative, variant, or analogue thereof, or, one or more serotypes of HIV inactivated by the nanoemulsion). When administered to a subject, a composition of the present invention stimulates an immune response against the immunogen within the subject. Although an understanding of the mechanism is not necessary to practice the present invention and the present invention is not limited to any particular mechanism of action, in some embodiments, generation of an immune response (e.g., resulting from administration of a composition comprising a nanoemulsion and an immunogen) provides total or partial immunity to the subject (e.g., from signs, symptoms or conditions of a disease (e.g., AIDS)). Without being bound to any specific theory, protection and/or immunity from disease (e.g., the ability of a subject's immune system to prevent or attenuate (e.g., suppress) a sign, symptom or condition of disease) after exposure to an immunogenic composition of the present invention is due to adaptive (e.g., acquired) immune responses (e.g., immune responses mediated by B and T cells following exposure to a NE comprising an immunogen of the present invention (e.g., immune responses that exhibit increased specificity and reactivity towards HIV). Thus, in some embodiments, the compositions and methods of the present invention are used prophylactically or therapeutically to prevent or attenuate a sign, symptom or condition associated with AIDS.

In some embodiments, a NE comprising an immunogen (e.g., a recombinant HIV protein) is administered alone. In some embodiments, a composition comprising a NE and an immunogen (e.g., a recombinant HIV protein) comprises one or more other agents (e.g., a pharmaceutically acceptable carrier, adjuvant, excipient, and the like). In some embodiments, a composition for stimulating an immune response of the present invention is administered in a manner to induce a humoral immune response. In some embodiments, a composition for stimulating an immune response of the present invention is administered in a manner to induce a cellular (e.g., cytotoxic T lymphocyte) immune response, rather than a humoral response. In some embodiments, a composition comprising a NE and an immunogen of the present invention induces both a cellular and humoral immune response.

The present invention is not limited by the type of NE utilized (e.g., in an immunogenic composition comprising an immunogen). Indeed, a variety of NE compositions are contemplated to be useful in the present invention.

For example, in some embodiments, a nanoemulsion comprises (i) an aqueous phase; (ii) an oil phase; and at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in a nanoemulsion of the present invention include, but are not limited to, one or more organic, and more particularly, organic phosphate based solvents, surfactants and detergents, cationic halogen containing compounds, germination enhancers, interaction enhancers, food additives (e.g., flavorings, sweetners, bulking agents, and the like) and pharmaceutically acceptable compounds. Certain exemplary embodiments of the various compounds contemplated for use in the compositions of the present invention are presented below.

A. Aqueous Phase

In certain preferred embodiments, a nanoemulsion comprises about 5 to 60, preferably 10 to 40, more preferably 15 to 30, vol. % aqueous phase, based on the total volume of the emulsion, although higher and lower amounts are contemplated. In preferred embodiments, the aqueous phase comprises water at a pH of about 4 to 10, preferably about 6 to 8. When the emulsions of the present invention contain a germination enhancer, the pH is preferably 6 to 8. The water is preferably deionized (hereinafter "DiH$_2$O") or distilled. In some embodiments the aqueous phase comprises phosphate buffered saline (PBS). In those embodiments of the present invention intended for administration to, or contact with, a subject (e.g., a subject vaccinated with a composition of the present invention), the aqueous phase, and any additional compounds provided in the aqueous phase, may further be sterile and pyrogen free.

B. Oil Phase and Solvents

In certain preferred embodiments, the oil phase (e.g., carrier oil) of a nanoemulsion comprises 30-90, preferably 60-80, and more preferably 60-70, vol. % of oil, based on the total volume of the emulsion, although higher and lower amounts are contemplated. Suitable oils include, but are not limited to, soybean oil, avocado oil, flaxseed oil, coconut oil, cottonseed oil, squalene oil, olive oil, canola oil, corn oil, rapeseed oil, safflower oil, sunflower oil, pine oil (e.g., 15%), Olestra oil, fish oils, flavor oils, water insoluble vitamins and mixtures thereof. In particularly preferred embodiments, soybean oil is used. Additional contemplated oils include motor oils, mineral oils, and butter. In preferred embodiments of the present invention, the oil phase is preferably distributed throughout the aqueous phase as droplets having a mean particle size in the range from about 1-2 microns, more preferably from 0.2 to 0.8, and most preferably about 0.8 microns. In other embodiments, the aqueous phase can be distributed in the oil phase. In some preferred embodiments, very small droplet sizes are utilized (e.g., less than 0.5 microns) to produce stable nanoemulsion compositions. It is contemplated that small droplet compositions also provide clear solutions, which may find desired use in certain product types.

In some embodiments, the oil phase comprises 3-15, preferably 5-10 vol. % of an organic solvent, based on the total volume of the emulsion, although higher and lower amounts are contemplated. Although an understanding of the mechanism is not necessary to practice the present invention and the present invention is not limited to any particular mechanism of action, it is contemplated that the organic phosphate-based solvents employed in an emulsion serves to disrupt and inactivate the pathogen (e.g., disrupt lipids in membranes or viral envelopes). Thus, any solvent that can remove sterols or phospholipids finds use in the emulsions of the present invention. Suitable organic solvents include, but are not limited to, organic phosphate based solvents or alcohols. In preferred embodiments, the organic phosphate based solvents include, but are not limited to, dialkyl- and trialkyl phosphates (e.g., tri-n-butyl phosphate (TBP)) in any combination. A particularly preferred trialkyl phosphate in certain embodiments comprises tri-n-butyl phosphate, which is a plasticizer. Moreover, in a preferred embodiment, each alkyl group of the di- or trialkyl phosphate has from one to ten or more carbon atoms, more preferably two to eight carbon atoms. The present invention also contemplates that each alkyl group of the di- or trialkyl phosphate may or may not be identical to one another. In certain embodiments, mixtures of different dialkyl and trialkyl phosphates can be employed. In those embodiments comprising one or more alcohols as solvents, such solvents include, but are not limited to, methanol, ethanol, propanol and octanol. In a particularly preferred embodiment, the alcohol is ethanol. In those embodiments of the present invention intended for consumption by, or contact to, a host, the oil phase, and any additional compounds provided in the oil phase, may further be sterile and pyrogen free.

C. Surfactants and Detergents

In some embodiments, a nanoemulsion further comprises one or more surfactants or detergents (e.g., from about 3 to 15%, and preferably about 10%, although higher and lower amounts are contemplated). While the present invention is not limited to any particular mechanism, and an understanding of the mechanism is not required to practice the present invention, it is contemplated that surfactants help to stabilize the compositions (e.g., used to generate an immune response in a subject (e.g., used as a vaccine). Both non-ionic (non-anionic) and ionic surfactants are contemplated. Additionally, surfactants from the BRIJ family of surfactants find use in the compositions of the present invention. The surfactant can be provided in either the aqueous or the oil phase. Surfactants suitable for use with the emulsions include a variety of anionic and nonionic surfactants, as well as other emulsifying compounds that are capable of promoting the formation of oil-in-water emulsions. In general, emulsifying compounds are relatively hydrophilic, and blends of emulsifying compounds can be used to achieve the necessary qualities. In some formulations, nonionic surfactants have advantages over ionic emulsifiers in that they are substantially more compatible with a broad pH range and often form more stable emulsions than do ionic (e.g., soap-type) emulsifiers. Thus, in certain preferred embodiments, a nanoemulsion comprises one or more non-ionic surfactants such as a polysorbate surfactants (e.g., polyoxyethylene ethers), polysorbate detergents, pheoxypolyethoxyethanols, and the like. Examples of polysorbate detergents useful in the present invention include, but are not limited to, TWEEN 20, TWEEN 40, TWEEN 60, TWEEN 80, etc.

TWEEN 60 (polyoxyethylenesorbitan monostearate), together with TWEEN 20, TWEEN 40 and TWEEN 80, comprise polysorbates that are used as emulsifiers in a number of pharmaceutical compositions. In some embodiments of the present invention, these compounds are also used as co-components with adjuvants. TWEEN surfactants also appear to have virucidal effects on lipid-enveloped viruses (See e.g., Eriksson et al., Blood Coagulation and Fibtinolysis 5 (Suppl. 3):S37-S44 (1994)).

Examples of pheoxypolyethoxyethanols, and polymers thereof, useful in the present invention include, but are not limited to, TRITON (e.g., X-100, X-301, X-165, X-102, X-200), and TYLOXAPOL. TRITON X-100 is a strong non-ionic detergent and dispersing agent widely used to extract lipids and proteins from biological structures. It also has virucidal effect against broad spectrum of enveloped viruses (See e.g., Maha and Igarashi, Southeast Asian J. Trop. Med. Pub. Health 28:718 (1997); and Portocala et al., Virologie 27:261 (1976)). Due to this anti-viral activity, it is employed to inactivate viral pathogens in fresh frozen human plasma (See e.g., Horowitz et al., Blood 79:826 (1992)).

In particularly preferred embodiments, the surfactants TRITON X-100 (t-octylphenoxypolyethoxyethanol), and/or TYLOXAPOL are employed. Some other embodiments, employ spermicides (e.g., Nonoxynol-9). Additional surfactants and detergents useful in the compositions of the present invention may be ascertained from reference works (See e.g., McCutheon's Volume 1: Emulsions and Detergents—North American Edition, 2000).

D. Cationic Halogen Containing Compounds

In some embodiments, nanoemulsions (e.g., used in an immunogenic composition of the present invention) further comprise a cationic halogen containing compound (e.g., from about 0.5 to 1.0 wt. % or more, based on the total weight of the emulsion, although higher and lower amounts are contemplated). In preferred embodiments, the cationic halogen-containing compound is preferably premixed with the oil phase; however, it should be understood that the cationic halogen-containing compound may be provided in combination with the emulsion composition in a distinct formulation. Suitable halogen containing compounds may be selected, for example, from compounds comprising chloride, fluoride, bromide and iodide ions. In preferred embodiments, suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with an particular cationic containing compound.

E. Germination Enhancers

In other embodiments of the present invention, nanoemulsion compositions further comprise one or more germination enhancing compounds (e.g., from about 1 mM to 15 mM, and more preferably from about 5 mM to 10 mM, although higher and lower amounts are contemplated). In preferred embodiments, the germination enhancing compound is provided in the aqueous phase prior to formation of the emulsion. The present invention contemplates that when germination enhancers are added to the disclosed compositions the sporicidal properties of the compositions are enhanced. The present invention further contemplates that such germination enhancers initiate sporicidal activity near neutral pH (between pH 6-8, and preferably 7). Such neutral pH emulsions can be obtained, for example, by diluting with phosphate buffer saline (PBS) or by preparations of neutral emulsions. The sporicidal activity of the compositions preferentially occurs when the spores initiate germination.

In certain embodiments, suitable germination enhancing agents of the invention include, but are not limited to, α-amino acids comprising glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104, herein incorporated by reference in its entirety. In some embodiments, a mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, Inosine and $NH_4Cl$. In some embodiments, the compositions further comprise one or more common forms of growth media (e.g., trypticase soy broth, and the like) that additionally may or may not itself comprise germination enhancers and buffers.

The above compounds are merely exemplary germination enhancers and it is understood that other known germination enhancers will find use in the compositions of the present invention. A candidate germination enhancer should meet two criteria for inclusion in the compositions of the present invention: it should be capable of being associated with a nanoemulsion and it should increase the rate of germination of a target spore when incorporated in the emulsions of the present invention.

F. Interaction Enhancers

In still other embodiments, a nanoemulsion may comprise one or more compounds capable of increasing the interaction of the nanoemulsion (i.e., "interaction enhancer") with a target pathogen (e.g., with a bacterial membrane or viral envelope). In some embodiments, the interaction enhancer is premixed with the oil phase; however, in other embodiments the interaction enhancer is provided in combination with the compositions after emulsification. In certain preferred embodiments, the interaction enhancer is a chelating agent (e.g., ethylenediaminetetraacetic acid (EDTA) or ethylenebis(oxyethylenenitrilo)tetraacetic acid (EGTA) in a buffer (e.g., tris buffer)). It is understood that chelating agents are merely exemplary interaction enhancing compounds. Indeed, other agents that increase the interaction of a nanoemulsion with a pathogen are contemplated. In particularly preferred embodiments, the interaction enhancer is at a concentration of about 50 to about 250 μM, although higher and lower amounts are contemplated. One skilled in the art will be able to determine whether a particular agent has the desired function of acting as an interaction enhancer by applying such an agent in combination with a nanoemulsion composition of the present invention to a target pathogen and comparing the inactivation of the target when contacted by the admixture with inactivation of like targets by the composition of the present invention without the agent. For example, an agent that increases the interaction and thereby neutralizes (e.g., decreases or inhibits the growth of the pathogen) in comparison to that parameter in its absence is considered an interaction enhancer.

G. Other Components

In some embodiments, a nanoemulsion comprises one or more additional components that provide a desired property or functionality to the nanoemulsions. These components may be incorporated into the aqueous phase or the oil phase of the nanoemulsions and/or may be added prior to or following emulsification. For example, in some embodiments, the nanoemulsions further comprise phenols (e.g., triclosan, phenyl phenol), acidifying agents (e.g., citric acid (e.g., 1.5-6%), acetic acid, lemon juice), alkylating agents (e.g., sodium hydroxide (e.g., 0.3%)), buffers (e.g., citrate buffer, acetate buffer, and other buffers useful to maintain a specific pH), and halogens (e.g., polyvinylpyrrolidone, sodium hypochlorite, hydrogen peroxide).

Exemplary techniques for making a nanoemulsion (e.g., used to inactivate a pathogen and/or generation of an immunogenic composition of the present invention) are described below. Additionally, a number of specific, although exemplary, formulation recipes are also set forth below.

Formulation Techniques Nanoemulsions of the present invention can be formed using classic emulsion forming techniques. In brief, the oil phase is mixed with the aqueous phase under relatively high shear forces (e.g., using high hydraulic and mechanical forces) to obtain an oil-in-water nanoemulsion. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In preferred embodiments, compositions used in the methods of the present invention comprise droplets of an oily discontinuous phase dispersed in an aqueous continuous phase, such as water. In preferred embodiments, nanoemulsions of the present invention are stable, and do not decompose even after long storage periods (e.g., greater than one or more years). Furthermore, in some embodiments, nanoemulsions are stable (e.g., in some embodiments for greater than 3 months, in some embodiments for greater than 6 months, in some embodiments for greater than 12 months, in some embodiments for greater than 18 months) after combination with an immunogen (e.g., a pathogen). In preferred embodiments, nanoemulsions of the present invention are non-toxic and safe when administered (e.g., via spraying or contacting mucosal surfaces, swallowed, inhaled, etc.) to a subject.

In some embodiments, a portion of the emulsion may be in the form of lipid structures including, but not limited to, unilamellar, multilamellar, and paucliamellar lipid vesicles, micelles, and lamellar phases.

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious for inactivation of pathogens and is also non-irritating and non-toxic to mammalian subjects (e.g., and thus can be used for administration to a mucosal surface).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

Exemplary Formulations

The following description provides a number of exemplary emulsions including formulations for compositions BCTP and $X_8W_{60}PC$. BCTP comprises a water-in oil nanoemulsion, in which the oil phase was made from soybean oil, tri-n-butyl phosphate, and TRITON X-100 in 80% water. $X_8W_{60}PC$ comprises a mixture of equal volumes of BCTP with $W_{80}8P$. $W_{80}8P$ is a liposome-like compound made of glycerol monostearate, refined oya sterols (e.g., GENEROL sterols), TWEEN 60, soybean oil, a cationic ion halogen-containing CPC and peppermint oil. The GENEROL family are a group of a polyethoxylated soya sterols (Henkel Corporation, Ambler, Pa.). Exemplary emulsion formulations useful in the present invention are provided in Table 1. These particular formulations may be found in U.S. Pat. Nos. 5,700,679 (NN); 5,618,840; 5,549,901 ($W_{80}8P$); and 5,547,677, each of which is hereby incorporated by reference in their entireties. Certain other emulsion formulations are presented U.S. patent application Ser. No. 10/669,865, hereby incorporated by reference in its entirety.

The $X_8W_{60}PC$ emulsion is manufactured by first making the $W_{80}8P$ emulsion and BCTP emulsions separately. A mixture of these two emulsions is then re-emulsified to produce a fresh emulsion composition termed $X_8W_{60}PC$. Methods of producing such emulsions are described in U.S. Pat. Nos. 5,103,497 and 4,895,452 (each of which is herein incorporated by reference in their entireties).

TABLE 1

| | Oil Phase Formula | Water to Oil Phase Ratio (Vol/Vol) |
|---|---|---|
| BCTP | 1 vol. Tri(N-butyl)phosphate<br>1 vol. TRITON X-100<br>8 vol. Soybean oil | 4:1 |
| NN | 86.5 g Glycerol monooleate<br>60.1 ml Nonoxynol-9<br>24.2 g GENEROL 122<br>3.27 g Cetylpyridinium chloride<br>554 g Soybean oil | 3:1 |
| $W_{80}8P$ | 86.5 g Glycerol monooleate<br>21.2 g Polysorbate 60<br>24.2 g GENEROL 122<br>3.27 g Cetylpyddinium chloride<br>4 ml Peppermint oil<br>554 g Soybean oil | 3.2:1 |
| SS | 86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth in water) |

The compositions listed above are only exemplary and those of skill in the art will be able to alter the amounts of the components to arrive at a nanoemulsion composition suitable for the purposes of the present invention. Those skilled in the art will understand that the ratio of oil phase to water as well as the individual oil carrier, surfactant CPC and organic phosphate buffer, components of each composition may vary.

Although certain compositions comprising BCTP have a water to oil ratio of 4:1, it is understood that the BCTP may be formulated to have more or less of a water phase. For example, in some embodiments, there is 3, 4, 5, 6, 7, 8, 9, 10, or more parts of the water phase to each part of the oil phase. The same holds true for the $W_{80}8P$ formulation. Similarly, the ratio of Tri(N-butyl)phosphate:TRITON X-100:soybean oil also may be varied.

Although Table 1 lists specific amounts of glycerol monooleate, polysorbate 60, GENEROL 122, cetylpyridinium chloride, and carrier oil for $W_{80}8P$, these are merely exemplary. An emulsion that has the properties of $W_{80}8P$ may be formulated that has different concentrations of each of these components or indeed different components that will fulfill the same function. For example, the emulsion may have between about 80 to about 100 g of glycerol monooleate in the initial oil phase. In other embodiments, the emulsion may have between about 15 to about 30 g polysorbate 60 in the initial oil phase. In yet another embodiment the composition may comprise between about 20 to about 30 g of a GENEROL sterol, in the initial oil phase.

Individual components of nanoemulsions (e.g. in an immunogenic composition of the present invention) can function both to inactivate a pathogen as well as to contribute to the non-toxicity of the emulsions. For example, the active component in BCTP, TRITON-X100, shows less ability to inactivate a virus at concentrations equivalent to 11% BCTP. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. Furthermore, when all the components of BCTP are combined in one composition but are not in a nanoemulsion structure, the mixture is not as effective at inactivating a pathogen as when the components are in a nanoemulsion structure.

Numerous additional embodiments presented in classes of formulations with like compositions are presented below. The following compositions recite various ratios and mixtures of active components. One skilled in the art will appreciate that the below recited formulation are exemplary and that additional formulations comprising similar percent ranges of the recited components are within the scope of the present invention.

In certain embodiments of the present invention, a nanoemulsion comprises from about 3 to 8 vol. % of TYLOXAPOL, about 8 vol. % of ethanol, about 1 vol. % of cetylpyridinium chloride (CPC), about 60 to 70 vol. % oil (e.g., soybean oil), about 15 to 25 vol. % of aqueous phase (e.g., $DiH_2O$ or PBS), and in some formulations less than about 1 vol. % of 1N NaOH. Some of these embodiments comprise PBS. It is contemplated that the addition of 1N NaOH and/or PBS in some of these embodiments, allows the user to advantageously control the pH of the formulations, such that pH ranges from about 7.0 to about 9.0, and more preferably from about 7.1 to 8.5 are achieved. For example, one embodiment of the present invention comprises about 3 vol. % of TYLOXAPOL, about 8 vol. % of ethanol, about 1 vol. % of CPC, about 64 vol. % of soybean oil, and about 24 vol. % of $DiH_2O$ (designated herein as Y3EC). Another similar embodiment comprises about 3.5 vol. % of TYLOXAPOL, about 8 vol. % of ethanol, and about 1 vol. % of CPC, about 64 vol. % of soybean oil, and about 23.5 vol. % of $DiH_2O$ (designated herein as Y3.5EC). Yet another embodiment comprises about 3 vol. % of TYLOXAPOL, about 8 vol. % of ethanol, about 1 vol. % of CPC, about 0.067 vol. % of 1N NaOH, such that the pH of the formulation is about 7.1, about 64 vol. % of soybean oil, and about 23.93 vol. % of $DiH_2O$ (designated herein as Y3EC pH 7.1). Still another embodiment comprises about 3 vol. % of TYLOXAPOL, about 8 vol. % of ethanol, about 1 vol. % of CPC, about 0.67 vol. % of 1N NaOH, such that the pH of the formulation is about 8.5, and about 64 vol. % of soybean oil, and about 23.33 vol. % of $DiH_2O$ (designated herein as Y3EC pH 8.5). Another similar embodiment comprises about 4% TYLOXAPOL, about 8 vol. % ethanol, about 1% CPC, and about 64 vol. % of soybean oil, and about 23 vol. % of $DiH_2O$ (designated herein as Y4EC). In still another embodiment the formulation comprises about 8% TYLOXAPOL, about 8% ethanol, about 1 vol. % of CPC, and about 64 vol. % of soybean oil, and about 19 vol. % of $DiH_2O$ (designated herein as Y8EC). A further embodiment comprises about 8 vol. % of TYLOXAPOL, about 8 vol. % of ethanol, about 1 vol. % of CPC, about 64 vol. % of soybean oil, and about 19 vol. % of 1×PBS (designated herein as Y8EC PBS).

In some embodiments of the present invention, a nanoemulsion comprises about 8 vol. % of ethanol, and about 1 vol. % of CPC, and about 64 vol. % of oil (e.g., soybean oil), and about 27 vol. % of aqueous phase (e.g., $DiH_2O$ or PBS) (designated herein as EC).

In some embodiments, a nanoemulsion comprises from about 8 vol. % of sodium dodecyl sulfate (SDS), about 8 vol. % of tributyl phosphate (TBP), and about 64 vol. % of oil (e.g., soybean oil), and about 20 vol. % of aqueous phase (e.g., $DiH_2O$ or PBS) (designated herein as S8P).

In some embodiments, a nanoemulsion comprises from about 1 to 2 vol. % of TRITON X-100, from about 1 to 2 vol. % of TYLOXAPOL, from about 7 to 8 vol. % of ethanol, about 1 vol. % of cetylpyridinium chloride (CPC), about 64 to 57.6 vol. % of oil (e.g., soybean oil), and about 23 vol. % of aqueous phase (e.g., $DiH_2O$ or PBS). Additionally, some of these formulations further comprise about 5 mM of L-alanine/Inosine, and about 10 mM ammonium chloride. Some of these formulations comprise PBS. It is contemplated that the addition of PBS in some of these embodiments, allows the user to advantageously control the pH of the formulations. For example, one embodiment of the present invention comprises about 2 vol. % of TRITON X-100, about 2 vol. % of TYLOXAPOL, about 8 vol. % of ethanol, about 1 vol. % CPC, about 64 vol. % of soybean oil, and about 23 vol. % of aqueous phase $DiH_2O$. In another embodiment the formulation comprises about 1.8 vol. % of TRITON X-100, about 1.8 vol. % of TYLOXAPOL, about 7.2 vol. % of ethanol, about 0.9 vol. % of CPC, about 5 mM L-alanine/Inosine, and about 10 mM ammonium chloride, about 57.6 vol. % of soybean oil, and the remainder of 1×PBS (designated herein as 90% X2Y2EC/GE).

In alternative embodiments, a nanoemulsion comprises from about 5 vol. % of TWEEN 80, from about 8 vol. % of ethanol, from about 1 vol. % of CPC, about 64 vol. % of oil (e.g., soybean oil), and about 22 vol. % of $DiH_2O$ (designated herein as $W_{80}5EC$).

In still other embodiments of the present invention, a nanoemulsion comprises from about 5 vol. % of TWEEN 20, from about 8 vol. % of ethanol, from about 1 vol. % of CPC, about 64 vol. % of oil (e.g., soybean oil), and about 22 vol. % of $DiH_2O$ (designated herein as $W_{20}5EC$).

In still other embodiments of the present invention, a nanoemulsion comprises from about 2 to 8 vol. % of TRITON X-100, about 8 vol. % of ethanol, about 1 vol. % of CPC, about 60 to 70 vol. % of oil (e.g., soybean, or olive oil), and about 15 to 25 vol. % of aqueous phase (e.g., $DiH_2O$ or PBS). For example, the present invention contemplates formulations comprising about 2 vol. % of TRITON X-100, about 8 vol. % of ethanol, about 64 vol. % of soybean oil, and about 26 vol. % of $DiH_2O$ (designated herein as X2E). In other similar embodiments, a nanoemulsion comprises about 3 vol. % of TRITON X-100, about 8 vol. % of ethanol, about 64 vol. % of soybean oil, and about 25 vol. % of $DiH_2O$ (designated herein as X3E). In still further embodiments, the formulations comprise about 4 vol. % Triton of X-100, about 8 vol. % of ethanol, about 64 vol. % of soybean oil, and about 24 vol. % of $DiH_2O$ (designated herein as X4E). In yet other embodiments, a nanoemulsion comprises about 5 vol. % of TRITON X-100, about 8 vol. % of ethanol, about 64 vol. % of soybean oil, and about 23 vol. % of $DiH_2O$ (designated herein as X5E). In some embodiments, a nanoemulsion comprises about 6 vol. % of TRITON X-100, about 8 vol. % of ethanol, about 64 vol. % of soybean oil, and about 22 vol. % of DiH$_2$O (designated herein as X6E). In still further embodiments of the present invention, a nanoemulsion comprises about 8 vol. % of TRITON X-100, about 8 vol. % of ethanol, about 64 vol. % of soybean oil, and about 20 vol. % of DiH$_2$O (designated herein as X8E). In still further embodiments, a nanoemulsion comprises about 8 vol. % of TRITON X-100, about 8 vol. % of ethanol, about 64 vol. % of olive oil, and about 20 vol. % of DiH$_2$O (designated herein as X8E j). In yet another embodiment, a nanoemulsion comprises 8 vol. % of TRITON X-100, about 8 vol. % ethanol, about 1 vol. % CPC, about 64 vol. % of soybean oil, and about 19 vol. % of DiH$_2$O (designated herein as X8EC).

In alternative embodiments of the present invention, a nanoemulsion comprises from about 1 to 2 vol. % of TRITON X-100, from about 1 to 2 vol. % of TYLOXAPOL, from about 6 to 8 vol. % TBP, from about 0.5 to 1.0 vol. % of CPC, from about 60 to 70 vol. % of oil (e.g., soybean), and about 1 to 35 vol. % of aqueous phase (e.g., DiH$_2$O or PBS). Additionally, certain of these nanoemulsions may comprise from about 1 to 5 vol. % of trypticase soy broth, from about 0.5 to 1.5 vol. % of yeast extract, about 5 mM L-alanine/Inosine, about 10 mM ammonium chloride, and from about 20-40 vol. % of liquid baby formula. In some embodiments comprising liquid baby formula, the formula comprises a casein hydrolysate (e.g., Neutramigen, or Progestimil, and the like). In some of these embodiments, a nanoemulsion further comprises from about 0.1 to 1.0 vol. % of sodium thiosulfate, and from about 0.1 to 1.0 vol. % of sodium citrate. Other similar embodiments comprising these basic components employ phosphate buffered saline (PBS) as the aqueous phase. For example, one embodiment comprises about 2 vol. % of TRITON X-100, about 2 vol. % TYLOXAPOL, about 8 vol. % TBP, about 1 vol. % of CPC, about 64 vol. % of soybean oil, and about 23 vol. % of DiH$_2$O (designated herein as X2Y2EC). In still other embodiments, the inventive formulation comprises about 2 vol. % of TRITON X-100, about 2 vol. % TYLOXAPOL, about 8 vol. % TBP, about 1 vol. % of CPC, about 0.9 vol. % of sodium thiosulfate, about 0.1 vol. % of sodium citrate, about 64 vol. % of soybean oil, and about 22 vol. % of DiH$_2$O (designated herein as X2Y2PC STS1). In another similar embodiment, a nanoemulsion comprises about 1.7 vol. % TRITON X-100, about 1.7 vol. % of TYLOXAPOL, about 6.8 vol. % TBP, about 0.85% CPC, about 29.2% NEUTRAMIGEN, about 54.4 vol. % of soybean oil, and about 4.9 vol. % of DiH$_2$O (designated herein as 85% X2Y2PC/baby). In yet another embodiment of the present invention, a nanoemulsion comprises about 1.8 vol. % of TRITON X-100, about 1.8 vol. % of TYLOXAPOL, about 7.2 vol. % of TBP, about 0.9 vol. % of CPC, about 5 mM L-alanine/Inosine, about 10 mM ammonium chloride, about 57.6 vol. % of soybean oil, and the remainder vol. % of 0.1×PBS (designated herein as 90% X2Y2 PC/GE). In still another embodiment, a nanoemulsion comprises about 1.8 vol. % of TRITON X-100, about 1.8 vol. % of TYLOXAPOL, about 7.2 vol. % TBP, about 0.9 vol. % of CPC, and about 3 vol. % trypticase soy broth, about 57.6 vol. % of soybean oil, and about 27.7 vol. % of DiH$_2$O (designated herein as 90% X2Y2PC/TSB). In another embodiment of the present invention, a nanoemulsion comprises about 1.8 vol. % TRITON X-100, about 1.8 vol. % TYLOXAPOL, about 7.2 vol. % TBP, about 0.9 vol. % CPC, about 1 vol. % yeast extract, about 57.6 vol. % of soybean oil, and about 29.7 vol. % of DiH$_2$O (designated herein as 90% X2Y2PC/YE).

In some embodiments of the present invention, a nanoemulsion comprises about 3 vol. % of TYLOXAPOL, about 8 vol. % of TBP, and about 1 vol. % of CPC, about 60 to 70 vol. % of oil (e.g., soybean or olive oil), and about 15 to 30 vol. % of aqueous phase (e.g., DiH$_2$O or PBS). In a particular embodiment of the present invention, a nanoemulsion comprises about 3 vol. % of TYLOXAPOL, about 8 vol. % of TBP, and about 1 vol. % of CPC, about 64 vol. % of soybean, and about 24 vol. % of DiH$_2$O (designated herein as Y3PC).

In some embodiments of the present invention, a nanoemulsion comprises from about 4 to 8 vol. % of TRITON X-100, from about 5 to 8 vol. % of TBP, about 30 to 70 vol. % of oil (e.g., soybean or olive oil), and about 0 to 30 vol. % of aqueous phase (e.g., DiH$_2$O or PBS). Additionally, certain of these embodiments further comprise about 1 vol. % of CPC, about 1 vol. % of benzalkonium chloride, about 1 vol. % cetylpyridinium bromide, about 1 vol. % cetyldimethylethylammonium bromide, 500 µM EDTA, about 10 mM ammonium chloride, about 5 mM Inosine, and about 5 mM L-alanine. For example, in a certain preferred embodiment, a nanoemulsion comprises about 8 vol. % of TRITON X-100, about 8 vol. % of TBP, about 64 vol. % of soybean oil, and about 20 vol. % of DiH$_2$O (designated herein as X8P). In another embodiment of the present invention, a nanoemulsion comprises about 8 vol. % of TRITON X-100, about 8 vol. % of TBP, about 1% of CPC, about 64 vol. % of soybean oil, and about 19 vol. % of DiH$_2$O (designated herein as X8PC). In still another embodiment, a nanoemulsion comprises about 8 vol. % TRITON X-100, about 8 vol. % of TBP, about 1 vol. % of CPC, about 50 vol. % of soybean oil, and about 33 vol. % of DiH$_2$O (designated herein as ATB-X1001). In yet another embodiment, the formulations comprise about 8 vol. % of TRITON X-100, about 8 vol. % of TBP, about 2 vol. % of CPC, about 50 vol. % of soybean oil, and about 32 vol. % of DiH$_2$O (designated herein as ATB-X002). In some embodiments, a nanoemulsion comprises about 4 vol. % TRITON X-100, about 4 vol. % of TBP, about 0.5 vol. % of CPC, about 32 vol. % of soybean oil, and about 59.5 vol. % of DiH$_2$O (designated herein as 50% X8PC). In some embodiments, a nanoemulsion comprises about 8 vol. % of TRITON X-100, about 8 vol. % of TBP, about 0.5 vol. % CPC, about 64 vol. % of soybean oil, and about 19.5 vol. % of DiH$_2$O (designated herein as X8PC$_{1/2}$). In some embodiments of the present invention, a nanoemulsion comprises about 8 vol. % of TRITON X-100, about 8 vol. % of TBP, about 2 vol. % of CPC, about 64 vol. % of soybean oil, and about 18 vol. % of DiH$_2$O (designated herein as X8PC2). In other embodiments, a nanoemulsion comprises about 8 vol. % of TRITON X-100, about 8% of TBP, about 1% of benzalkonium chloride, about 50 vol. % of soybean oil, and about 33 vol. % of DiH$_2$O (designated herein as X8P BC). In an alternative embodiment of the present invention, a nanoemulsion comprises about 8 vol. % of TRITON X-100, about 8 vol. % of TBP, about 1 vol. % of cetylpyridinium bromide, about 50 vol. % of soybean oil, and about 33 vol. % of DiH$_2$O (designated herein as X8P CPB). In another exemplary embodiment of the present invention, a nanoemulsion comprises about 8 vol. % of TRITON X-100, about 8 vol. % of TBP, about 1 vol. % of cetyldimethylethylammonium bromide, about 50 vol. % of soybean oil, and about 33 vol. % of DiH$_2$O (designated herein as X8P CTAB). In still further embodiments, a nanoemulsion comprises about 8 vol. % of TRITON X-100, about 8 vol. % of TBP, about 1 vol. % of CPC, about 500 µM EDTA, about 64 vol. % of soybean oil, and about 15.8 vol. % DiH$_2$O (designated herein as X8PC EDTA). In some embodiments, a nanoemulsion comprises 8 vol. % of TRITON X-100, about 8 vol. % of TBP, about 1 vol. % of CPC, about 10 mM ammonium chloride, about 5 mM Inosine, about 5 mM L-alanine, about 64 vol. % of soybean oil, and about 19 vol. % of DiH$_2$O or PBS (designated herein as X8PC GE$_{1x}$). In another embodiment of the present invention, a nanoemulsion comprises about 5 vol. % of TRITON X-100, about 5% of TBP, about 1 vol. % of CPC, about 40 vol. % of soybean oil, and about 49 vol. % of DiH$_2$O (designated herein as X5P$_5$C).

In some embodiments of the present invention, a nanoemulsion comprises about 2 vol. % TRITON X-100, about 6 vol. % TYLOXAPOL, about 8 vol. % ethanol, about 64 vol. % of soybean oil, and about 20 vol. % of DiH$_2$O (designated herein as X2Y6E).

In an additional embodiment of the present invention, a nanoemulsion comprises about 8 vol. % of TRITON X-100, and about 8 vol. % of glycerol, about 60 to 70 vol. % of oil (e.g., soybean or olive oil), and about 15 to 25 vol. % of aqueous phase (e.g., DiH$_2$O or PBS). Certain nanoemulsion compositions (e.g., used to generate an immune response (e.g., for use as a vaccine) comprise about 1 vol. % L-ascorbic acid. For example, one particular embodiment comprises about 8 vol. % of TRITON X-100, about 8 vol. % of glycerol, about 64 vol. % of soybean oil, and about 20 vol. % of DiH$_2$O (designated herein as X8G). In still another embodiment, a nanoemulsion comprises about 8 vol. % of TRITON X— 100, about 8 vol. % of glycerol, about 1 vol. % of L-ascorbic acid, about 64 vol. % of soybean oil, and about 19 vol. % of DiH$_2$O (designated herein as X8GV$_c$).

In still further embodiments, a nanoemulsion comprises about 8 vol. % of TRITON X-100, from about 0.5 to 0.8 vol. % of TWEEN 60, from about 0.5 to 2.0 vol. % of CPC, about 8 vol. % of TBP, about 60 to 70 vol. % of oil (e.g., soybean or olive oil), and about 15 to 25 vol. % of aqueous phase (e.g., DiH$_2$O or PBS). For example, in one particular embodiment a nanoemulsion comprises about 8 vol. % of TRITON X-100, about 0.70 vol. % of TWEEN 60, about 1 vol. % of CPC, about 8 vol. % of TBP, about 64 vol. % of soybean oil, and about 18.3 vol. % of DiH$_2$O (designated herein as X8W60PC$_1$). In some embodiments, a nanoemulsion comprises about 8 vol. % of TRITON X-100, about 0.71 vol. % of TWEEN 60, about 1 vol. % of CPC, about 8 vol. % of TBP, about 64 vol. % of soybean oil, and about 18.29 vol. % of DiH$_2$O (designated herein as W60$_{0.7}$X8PC). In yet other embodiments, a nanoemulsion comprises from about 8 vol. % of TRITON X-100, about 0.7 vol. % of TWEEN 60, about 0.5 vol. % of CPC, about 8 vol. % of TBP, about 64 to 70 vol. % of soybean oil, and about 18.8 vol. % of DiH$_2$O (designated herein as X8W60PC$_2$). In still other embodiments, a nanoemulsion comprises about 8 vol. % of TRITON X-100, about 0.71 vol. % of TWEEN 60, about 2 vol. % of CPC, about 8 vol. % of TBP, about 64 vol. % of soybean oil, and about 17.3 vol. % of DiH$_2$O. In another embodiment of the present invention, a nanoemulsion comprises about 0.71 vol. % of TWEEN 60, about 1 vol. % of CPC, about 8 vol. % of TBP, about 64 vol. % of soybean oil, and about 25.29 vol. % of DiH$_2$O (designated herein as W60$_{0.7}$PC).

In another embodiment of the present invention, a nanoemulsion comprises about 2 vol. % of dioctyl sulfosuccinate, either about 8 vol. % of glycerol, or about 8 vol. % TBP, in addition to, about 60 to 70 vol. % of oil (e.g., soybean or olive oil), and about 20 to 30 vol. % of aqueous phase (e.g., DiH$_2$O or PBS). For example, in some embodiments, a nanoemulsion comprises about 2 vol. % of dioctyl sulfosuccinate, about 8 vol. % of glycerol, about 64 vol. % of soybean oil, and about 26 vol. % of DiH$_2$O (designated herein as D2G). In another related embodiment, a nanoemulsion comprises about 2 vol. % of dioctyl sulfosuccinate, and about 8 vol. % of TBP, about 64 vol. % of soybean oil, and about 26 vol. % of D1H$_2$O (designated herein as D2P).

In still other embodiments of the present invention, a nanoemulsion comprises about 8 to 10 vol. % of glycerol, and about 1 to 10 vol. % of CPC, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprises about 1 vol. % of L-ascorbic acid. For example, in some embodiments, a nanoemulsion comprises about 8 vol. % of glycerol, about 1 vol. % of CPC, about 64 vol. % of soybean oil, and about 27 vol. % of DiH$_2$O (designated herein as GC). In some embodiments, a nanoemulsion comprises about 10 vol. % of glycerol, about 10 vol. % of CPC, about 60 vol. % of soybean oil, and about 20 vol. % of DiH$_2$O (designated herein as GC10). In still another embodiment of the present invention, a nanoemulsion comprises about 10 vol. % of glycerol, about 1 vol. % of CPC, about 1 vol. % of L-ascorbic acid, about 64 vol. % of soybean or oil, and about 24 vol. % of DiH$_2$O (designated herein as GCV$_c$).

In some embodiments of the present invention, a nanoemulsion comprises about 8 to 10 vol. % of glycerol, about 8 to 10 vol. % of SDS, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprise about 1 vol. % of lecithin, and about 1 vol. % of p-Hydroxybenzoic acid methyl ester. Exemplary embodiments of such formulations comprise about 8 vol. % SDS, 8 vol. % of glycerol, about 64 vol. % of soybean oil, and about 20 vol. % of DiH$_2$O (designated herein as S8G). A related formulation comprises about 8 vol. % of glycerol, about 8 vol. % of SDS, about 1 vol. % of lecithin, about 1 vol. % of p-Hydroxybenzoic acid methyl ester, about 64 vol. % of soybean oil, and about 18 vol. % of DiH$_2$O (designated herein as S8GL1B1).

In yet another embodiment of the present invention, a nanoemulsion comprises about 4 vol. % of TWEEN 80, about 4 vol. % of TYLOXAPOL, about 1 vol. % of CPC, about 8 vol. % of ethanol, about 64 vol. % of soybean oil, and about 19 vol. % of DiH$_2$O (designated herein as W$_{80}$4Y4EC).

In some embodiments of the present invention, a nanoemulsion comprises about 0.01 vol. % of CPC, about 0.08 vol. % of TYLOXAPOL, about 10 vol. % of ethanol, about 70 vol. % of soybean oil, and about 19.91 vol. % of DiH$_2$O (designated herein as Y.08EC.01).

In yet another embodiment of the present invention, a nanoemulsion comprises about 8 vol. % of sodium lauryl sulfate, and about 8 vol. % of glycerol, about 64 vol. % of soybean oil, and about 20 vol. % of DiH$_2$O (designated herein as SLS8G).

The specific formulations described above are simply examples to illustrate the variety of nanoemulsions that find use (e.g., to inactivate and/or neutralize a pathogen, and for generating an immune response in a subject (e.g., for use as a vaccine)) in the present invention. The present invention contemplates that many variations of the above formulations, as well as additional nanoemulsions, find use in the methods of the present invention. Candidate emulsions can be easily tested to determine if they are suitable. First, the desired ingredients are prepared using the methods described herein, to determine if an emulsion can be formed. If an emulsion cannot be formed, the candidate is rejected. For example, a candidate composition made of 4.5% sodium thiosulfate, 0.5% sodium citrate, 10% n-butanol, 64% soybean oil, and 21% DiH$_2$O does not form an emulsion.

Second, the candidate emulsion should form a stable emulsion. An emulsion is stable if it remains in emulsion form for a sufficient period to allow its intended use (e.g., to generate an immune response in a subject). For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% TWEEN 10, 1% CPC, 64% soybean oil, and 22% DiH$_2$O does not form a stable emulsion. Nanoemulsions that have been shown to be stable include, but are not limited to, 8 vol. % of TRITON X-100, about 8 vol. % of TBP, about 64 vol. % of soybean oil, and about 20 vol. % of DiH$_2$O (designated herein as X8P); 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC); 0.08% Triton X-100, 0.08% Glycerol, 0.01% Cetylpyridinium Chloride, 99% Butter, and 0.83% diH$_2$O (designated herein as 1% X8GC Butter); 0.8% Triton X-100, 0.8% Glycerol, 0.1% Cetylpyridinium Chloride, 6.4% Soybean Oil, 1.9% diH$_2$O, and 90% Butter (designated herein as 10% X8GC Butter); 2% W$_{20}$5EC, 1% Natrosol 250L NF, and 97% diH$_2$O (designated herein as 2% W$_{20}$5EC L GEL); 1% Cetylpyridinium Chloride, 5% TWEEN 20, 8% Ethanol, 64% 70 Viscosity Mineral Oil, and 22% diH$_2$O (designated herein as W$_{20}$5EC 70 Mineral Oil); 1% Cetylpyridinium Chloride, 5% TWEEN 20, 8% Ethanol, 64% 350 Viscosity Mineral Oil, and 22% diH$_2$O (designated herein as W$_{20}$5EC 350 Mineral Oil). In some embodiments, nanoemulsions of the present invention are stable for over a week, over a month, or over a year.

Third, the candidate emulsion should have efficacy for its intended use. For example, a nanoemulsion should inactivate (e.g., kill or inhibit growth of) a pathogen to a desired level (e.g., 1 log, 2 log, 3 log, 4 log, . . . reduction). Using the methods described herein, one is capable of determining the suitability of a particular candidate emulsion against the desired pathogen. Generally, this involves exposing the pathogen to the emulsion for one or more time periods in a side-by-side experiment with the appropriate control samples (e.g., a negative control such as water) and determining if, and to what degree, the emulsion inactivates (e.g., kills and/or neutralizes) the microorganism. For example, a candidate composition made of 1% ammonium chloride, 5% TWEEN 20, 8% ethanol, 64% soybean oil, and 22% DiH$_2$O was shown not to be an effective emulsion. The following candidate emulsions were shown to be effective using the methods described herein: 5% TWEEN 20, 5% Cetylpyridinium Chloride, 10% Glycerol, 60% Soybean Oil, and 20% diH$_2$O (designated herein as W$_{20}$5GC5); 1% Cetylpyridinium Chloride, 5% TWEEN 20, 10% Glycerol, 64% Soybean Oil, and 20% diH$_2$O (designated herein as W$_{20}$5GC); 1% Cetylpyridinium Chloride, 5% TWEEN 20, 8% Ethanol, 64% Olive Oil, and 22% diH$_2$O (designated herein as W$_{20}$5EC Olive Oil); 1% Cetylpyridinium Chloride, 5% TWEEN 20, 8% Ethanol, 64% Flaxseed Oil, and 22% diH$_2$O (designated herein as W$_{20}$5EC Flaxseed Oil); 1% Cetylpyridinium Chloride, 5% TWEEN 20, 8% Ethanol, 64% Corn Oil, and 22% diH$_2$O (designated herein as W$_{20}$5EC Corn Oil); 1% Cetylpyridinium Chloride, 5% TWEEN 20, 8% Ethanol, 64% Coconut Oil, and 22% diH$_2$O (designated herein as W$_{20}$5EC Coconut Oil); 1% Cetylpyridinium Chloride, 5% TWEEN 20, 8% Ethanol, 64% Cottonseed Oil, and 22% diH$_2$O (designated herein as W$_{20}$5EC Cottonseed Oil); 8% Dextrose, 5% TWEEN 10, 1% Cetylpyridinium Chloride, 64% Soybean Oil, and 22% diH$_2$O (designated herein as W$_{20}$5C Dextrose); 8% PEG 200, 5% TWEEN 10, 1% Cetylpyridinium Chloride, 64% Soybean Oil, and 22% diH$_2$O (designated herein as W$_{20}$5C PEG 200); 8% Methanol, 5% TWEEN 10, 1% Cetylpyridinium Chloride, 64% Soybean Oil, and 22% diH$_2$O (designated herein as W$_{20}$5C Methanol); 8% PEG 1000, 5% TWEEN 10, 1% Cetylpyridinium Chloride, 64% Soybean Oil, and 22% diH$_2$O (designated herein as W$_{20}$5C PEG 1000); 2% W$_{20}$5EC, 2% Natrosol 250H NF, and 96% diH$_2$O (designated herein as 2% W$_{20}$5EC Natrosol 2, also called 2% W$_{20}$5EC GEL); 2% W$_{20}$5EC, 1% Natrosol 250H NF, and 97% diH$_2$O (designated herein as 2% W$_{20}$5EC Natrosol 1); 2% W$_{20}$5EC, 3% Natrosol 250H NF, and 95% diH$_2$O (designated herein as 2% W$_{20}$5EC Natrosol 3); 2% W$_{20}$5EC, 0.5% Natrosol 250H NF, and 97.5% diH$_2$O (designated herein as 2% W$_{20}$5EC Natrosol 0.5); 2% W$_{20}$5EC, 2% Methocel A, and 96% diH$_2$O (designated herein as 2% W$_{20}$5EC Methocel A); 2% W$_{20}$5EC, 2% Methocel K, and 96% diH$_2$O (designated herein as 2% W$_{20}$5EC Methocel K); 2% Natrosol, 0.1% X8PC, 0.1×PBS, 5 mM L-alanine, 5 mM Inosine, 10 mM Ammonium Chloride, and diH$_2$O (designated herein as 0.1% X8PC/GE+2% Natrosol); 2% Natrosol, 0.8% Triton X-100, 0.8% Tributyl Phosphate, 6.4% Soybean Oil, 0.1% Cetylpyridinium Chloride, 0.1×PBS, 5 mM L-alanine, 5 mM Inosine, 10 mM Ammonium Chloride, and diH$_2$O (designated herein as 10% X8PC/GE+2% Natrosol); 1% Cetylpyridinium Chloride, 5% TWEEN 20, 8% Ethanol, 64% Lard, and 22% diH$_2$O (designated herein as W$_{20}$5EC Lard); 1% Cetylpyridinium Chloride, 5% TWEEN 20, 8% Ethanol, 64% Mineral Oil, and 22% diH$_2$O (designated herein as W$_{20}$5EC Mineral Oil); 0.1% Cetylpyridinium Chloride, 2% Nerolidol, 5% TWEEN 20, 10% Ethanol, 64% Soybean Oil, and 18.9% diH$_2$O (designated herein as W$_{20}$5EC$_{0.1}$N); 0.1% Cetylpyridinium Chloride, 2% Farnesol, 5% TWEEN 20, 10% Ethanol, 64% Soybean Oil, and 18.9% diH$_2$O (designated herein as W$_{20}$5EC$_{0.1}$F); 0.1% Cetylpyridinium Chloride, 5% TWEEN 20, 10% Ethanol, 64% Soybean Oil, and 20.9% diH$_2$O (designated herein as W$_{20}$5EC$_{0.1}$); 10% Cetylpyridinium Chloride, 8% Tributyl Phosphate, 8% Triton X-100, 54% Soybean Oil, and 20% diH$_2$O (designated herein as X8PC$_{10}$); 5% Cetylpyridinium Chloride, 8% Triton X-100, 8% Tributyl Phosphate, 59% Soybean Oil, and 20% diH$_2$O (designated herein as X8PC$_5$); 0.02% Cetylpyridinium Chloride, 0.1% TWEEN 20, 10% Ethanol, 70% Soybean Oil, and 19.88% diH$_2$O (designated herein as W$_{20}$0.1EC$_{0.02}$); 1% Cetylpyridinium Chloride, 5% TWEEN 20, 8% Glycerol, 64% Mobil 1, and 22% diH$_2$O (designated herein as W$_{20}$5GC Mobil 1); 7.2% Triton X-100, 7.2% Tributyl Phosphate, 0.9% Cetylpyridinium Chloride, 57.6% Soybean Oil, 0.1×PBS, 5 mM L-alanine, 5 mM Inosine, 10 mM Ammonium Chloride, and 25.87% diH$_2$O (designated herein as 90% X8PC/GE); 7.2% Triton X-100, 7.2% Tributyl Phosphate, 0.9% Cetylpyridinium Chloride, 57.6% Soybean Oil, 1% EDTA, 5 mM L-alanine, 5 mM Inosine, 10 mM Ammonium Chloride, 0.1×PBS, and diH$_2$O (designated herein as 90% X8PC/GE EDTA); and 7.2% Triton X-100, 7.2% Tributyl Phosphate, 0.9% Cetylpyridinium Chloride, 57.6% Soybean Oil, 1% Sodium Thiosulfate, 5 mM L-alanine, 5 mM Inosine, 10 mM Ammonium Chloride, 0.1×PBS, and diH$_2$O (designated herein as 90% X8PC/GE STS).

In preferred embodiments of the present invention, the nanoemulsions are non-toxic (e.g., to humans, plants, or animals), non-irritant (e.g., to humans, plants, or animals), and non-corrosive (e.g., to humans, plants, or animals or the environment), while possessing potency against a broad range of microorganisms including bacteria, fungi, viruses, and spores. While a number of the above described nanoemulsions meet these qualifications, the following description provides a number of preferred non-toxic, non-irritant, non-corrosive, anti-microbial nanoemulsions of the present invention (hereinafter in this section referred to as "non-toxic nanoemulsions").

In some embodiments the non-toxic nanoemulsions comprise surfactant lipid preparations (SLPs) for use as broad-spectrum antimicrobial agents that are effective against bacteria and their spores, enveloped viruses, and fungi. In preferred embodiments, these SLPs comprises a mixture of oils, detergents, solvents, and cationic halogen-containing compounds in addition to several ions that enhance their biocidal activities. These SLPs are characterized as stable, non-irritant, and non-toxic compounds compared to commercially available bactericidal and sporicidal agents, which are highly irritant and/or toxic.

Ingredients for use in the non-toxic nanoemulsions include, but are not limited to: detergents (e.g., TRITON X-100 (5-15%) or other members of the TRITON family, TWEEN 60 (0.5-2%) or other members of the TWEEN family, or TYLOXAPOL (1-10%)); solvents (e.g., tributyl phosphate (5-15%)); alcohols (e.g., ethanol (5-15%) or glycerol (5-15%)); oils (e.g., soybean oil (40-70%)); cationic halogen-containing compounds (e.g., cetylpyridinium chloride (0.5-2%), cetylpyridinium bromide (0.5-2%)), or cetyldimethylethyl ammonium bromide (0.5-2%)); quaternary ammonium compounds (e.g., benzalkonium chloride (0.5-2%), N-alkyldimethylbenzyl ammonium chloride (0.5-2%)); ions (calcium chloride (1 mM-40 mM), ammonium chloride (1 mM-20 mM), sodium chloride (5 mM-200 mM), sodium phosphate (1 mM-20 mM)); nucleosides (e.g., inosine (50 µM-20 mM)); and amino acids (e.g., L-alanine (50 µM-20 mM)). Emulsions are prepared, for example, by mixing in a high shear mixer for 3-10 minutes. The emulsions may or may not be heated before mixing at 82° C. for 1 hour.

Quaternary ammonium compounds for use in the present include, but are not limited to, N-alkyldimethyl benzyl ammonium saccharinate; 1,3,5-Triazine-1,3,5(2H,4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy) ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-($C_{8-10}$)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis(alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

In general, the preferred non-toxic nanoemulsions are characterized by the following: they are approximately 200-800 nm in diameter, although both larger and smaller diameter nanoemulsions are contemplated; the charge depends on the ingredients; they are stable for relatively long periods of time (e.g., up to two years), with preservation of their biocidal activity; they are non-irritant and non-toxic compared to their individual components due, at least in part, to their oil contents that markedly reduce the toxicity of the detergents and the solvents; they are effective at concentrations as low as 0.1%; they have antimicrobial activity against most vegetative bacteria (including Gram-positive and Gram-negative organisms), fungi, and enveloped and nonenveloped viruses in 15 minutes (e.g., 99.99% killing); and they have sporicidal activity in 1-4 hours (e.g., 99.99% killing) when produced with germination enhancers.

The present invention is not limited by the type (e.g., serotype, group, or lade) of HIV used or immunogenic protein derived therefrom. For example, there are currently two types of HIV: HIV-1 and HIV-2. Both types are transmitted by sexual contact, through blood, and from mother to child, and they appear to cause clinically indistinguishable AIDS. However, it seems that HIV-2 is less easily transmitted, and the period between initial infection and illness is longer in the case of HIV-2. Worldwide, the predominant virus is HIV-1, and generally when people refer to HIV without specifying the type of virus they will be referring to HIV-1. The relatively uncommon HIV-2 type is concentrated in West Africa and is rarely found elsewhere.

Different levels of HIV classification exist. Each type is divided into groups, and each group is divided into subtypes and circulating recombinant forms (CRFs). The strains of HIV-1 can be classified into three groups: the "major" group M, the "outlier" group 0 and the "new" group N.

Within group M there are known to be at least nine genetically distinct subtypes (or clades) of HIV-1. These are subtypes A, B, C, D, F, G, H, J and K.

Any one of these or yet to be identified or generated serotypes, groups, or clades may be used in an immunogenic composition comprising a NE of the present invention.

In some embodiments, the immunogen may comprise one or more antigens derived from a pathogen (e.g., HIV). For example, in some embodiments, the immunogen is a purified, recombinant, synthetic, or otherwise isolated protein (e.g., added to the NE to generate an immunogenic composition). Similarly, the immunogenic protein may be a derivative, analogue or otherwise modified form of a protein from a pathogen. The present invention is not limited by the type of protein (e.g., derived from HIV) used for generation of an immunogenic composition of the present invention. Indeed, a variety of immunogenic proteins may be used including, but not limited to, gp160, gp120, gp41, Tat, and Nef, as well as analogues, derivatives and modified forms thereof.

For example, HIV proteins of the present invention may be used in their native conformation, or more preferably, may be modified for vaccine use. These modifications may either be required for technical reasons relating to the method of purification, or they may be used to biologically inactivate one or several functional properties of HIV protein. Thus the invention encompasses derivatives of HIV proteins which may be, for example mutated proteins (e.g., that has undergone deletion, addition or substitution of one or more amino acids using well known techniques for site directed mutagenesis or any other conventional method.

For example, a HIV protein may be mutated so that it is biologically inactive while maintaining its immunogenic epitopes (See, e.g., Clements, Virology 235: 48-64, 1997).

Additionally, HIV proteins of the present invention may be modified by chemical methods during the purification process to render the proteins stable and monomeric. One method to prevent oxidative aggregation of a HIV protein is the use of chemical modifications of the protein's thiol groups. In a first step the disulphide bridges are reduced by treatment with a reducing agent such as DTT, β-mercaptoethanol, or gluthathione. In a second step the resulting thiols are blocked by reaction with an alkylating agent (e.g., the protein can be carboxyamidated/carbamidomethylated using iodoacetamide).

Each HIV serotype, group or lade alone, or in combination with another family member, may be used to generate a composition comprising a NE and an immunogen (e.g., used to generate an immune response) of the present invention. A composition comprising a NE and immunogen may comprise one or more serotypes, groups or clades of HIV. Additionally, a composition comprising a NE and immunogen may comprise one or more serotypes, groups or clades of HIV, and, in addition, one or more strains of a non-HIV immunogen (e.g., a virus such as West Nile virus, Avian Influenza virus, Ebola virus, HSV, HPV, HCV, etc. or an immunogenic epitope thereof).

The present invention is not limited by the particular formulation of a composition comprising a NE and immunogen of the present invention. Indeed, a composition comprising a NE and immunogen of the present invention may comprise one or more different agents in addition to the NE and immunogen. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a NE and immunogen of the present invention comprises an agent and/or co-factor that enhance the ability of the immunogen to induce an immune response (e.g., an adjuvant). In some preferred embodiments, the presence of one or more co-factors or agents reduces the amount of immunogen required for induction of an immune response (e.g., a protective immune response (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition) comprising a NE and immunogen). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In some embodiments, it is preferred that a composition comprising a NE and immunogen of the present invention comprises one or more adjuvants that induce a Th1-type response. However, in other embodiments, it will be preferred that a composition comprising a NE and immunogen of the present invention comprises one or more adjuvants that induce a Th2-type response.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells. However in other embodiments, Th2-type cytokines can be induced thereby promoting a Th2 type antigen-specific immune response.

Cytokines play a role in directing the T cell response. Helper (CD4$^+$) T cells orchestrate the immune response of mammals through production of soluble factors that act on other immune system cells, including B and other T cells. Most mature CD4+ T helper cells express one of two cytokine profiles: Th1 or Th2. Th1-type CD4+ T cells secrete IL-2, IL-3, IFN-γ, GM-CSF and high levels of TNF-αc. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in some preferred embodiments, the present invention provides a method of stimulating a Th1-type immune response in a subject comprising administering to a subject a composition comprising a NE and an immunogen. However, in other preferred embodiments, the present invention provides a method of stimulating a Th2-type immune response in a subject comprising administering to a subject a composition comprising a NE and an immunogen. In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree *Quillaja Saponaria* Molina), and fractions thereof (See, e.g., U.S. Pat. No. 5,057,540; Kensil, Crit. Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant in the present invention. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a NE solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an *E. Coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising a NE and immunogen of the present invention.

Additional examples of adjuvants that find use in the present invention include poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Adjuvants may be added to a composition comprising a NE and an immunogen, or, the adjuvant may be formulated with carriers, for example liposomes, or metallic salts (e.g., aluminium salts (e.g., aluminium hydroxide)) prior to combining with or co-administration with a composition comprising a NE and an immunogen.

In some embodiments, a composition comprising a NE and an immunogen comprises a single adjuvant. In other embodiments, a composition comprising a NE and an immunogen comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising a NE and an immunogen of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a NE and immunogen) enhances induction of an immune response in a subject (e.g., administered a composition of the present invention) due to an increase in duration and/or amount of exposure to an immunogen that a subject experiences when a mucoadhesive is used compared to the duration and/or amount of exposure to an immunogen in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a NE and an immunogen of the present invention can be used therapeutically (e.g., to enhance an immune response) or as a prophylactic (e.g., for immunization (e.g., to prevent signs or symptoms of disease)). A composition comprising a NE and an immunogen of the present invention can be administered to a subject via a number of different delivery routes and methods.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some preferred embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science and Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the preferred route of administration as it has been shown that mucosal administration of antigens has a greater efficacy of inducing protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). More advantageously, in further preferred embodiments, in addition to inducing mucosal immune responses, mucosal vaccination also induces systemic immunity. In some embodiments, non-parenteral administration (e.g., mucosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a NE and an immunogen of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition comprising a NE and immunogen is provided. Enteric formulations such as gastro resistant capsules for oral administration, suppositories for rectal or vaginal administration also form part of this invention. Compositions of the present invention may also be administered via the oral route. Under these circumstances, a composition comprising a NE and an immunogen may comprise a pharmaceutically acceptable excipient and/or include alkaline buffers, or enteric capsules. Formulations for nasal delivery may include those with dextran or cyclodextran and saponin as an adjuvant.

Compositions of the present invention may also be administered via a vaginal route. In such cases, a composition comprising a NE and an immunogen may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, a composition comprising a NE and an immunogen may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response (e.g., using a composition comprising a NE and immunogen of the present invention).

For example, in some embodiments, a composition comprising a NE and an immunogen is administered to a mucosal surface of a subject in either a priming or boosting vaccination regime. Alternatively, in some embodiments, a composition comprising a NE and an immunogen is administered systemically in either a priming or boosting vaccination regime. In some embodiments, a composition comprising a NE and an immunogen is administered to a subject in a priming vaccination regimen via mucosal administration and a boosting regimen via systemic administration. In some embodiments, a composition comprising a NE and an immunogen is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising a NE and an immunogen may be used for both prophylactic and therapeutic purposes.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. 111, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colorado; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising a NE and an immunogen of the present invention may be used to protect and/or treat a subject susceptible to, or suffering from, a disease by means of administering a compositions comprising a NE and an immunogen by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. No. 4,596,556; U.S. Pat. No. 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism. In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition of the present invention may be formulated for administration by any route, such as mucosal, oral, topical, parenteral or other route described herein. The compositions may be in any one or more different forms including, but not limited to, tablets, capsules, powders, granules, lozenges, foams, creams or liquid preparations.

Topical formulations of the present invention may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl)pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins.

Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present invention may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the NE and immunogen of the formulation. In some embodiments, immunostimulatory compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, a composition comprising a NE and an immunogen is co-administered with one or more antibiotics. For example, one or more antibiotics may be administered with, before and/or after administration of a composition comprising a NE and an immunogen. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polymyxin and colistimethate and the antifungals nystatin and amphotericin B); agents that affect the ribosomal subunits to inhibit protein synthesis (e.g., chloramphenicol, the tetracyclines, erythromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gancyclovir, vidarabine, and acyclovir which act to inhibit viral enzymes essential for DNA synthesis. Various combinations of antimicrobials may be employed.

The present invention also includes methods involving co-administration of a composition comprising a NE and an immunogen with one or more additional active and/or immunostimulatory agents (e.g., a composition comprising a NE and a different immunogen, an antibiotic, anti-oxidant, etc.). Indeed, it is a further aspect of this invention to provide methods for enhancing prior art immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

In some embodiments, a composition comprising a NE and immunogen is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an immunogen or organism from which the immunogen is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of a composition comprising a NE and immunogen of the present invention) may have a stronger immune response to an immunogen than a subject administered a composition via just one route.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In preferred embodiments, a composition comprising a NE and an immunogen of the present invention comprises a suitable amount of the immunogen to induce an immune response in a subject when administered to the subject. In preferred embodiments, the immune response is sufficient to provide the subject protection (e.g., immune protection) against a subsequent exposure to the immunogen or the microorganism (e.g., bacteria or virus) from which the immunogen was derived. The present invention is not limited by the amount of immunogen used. In some preferred embodiments, the amount of immunogen (e.g., virus or bacteria neutralized by the NE, or, recombinant protein) in a composition comprising a NE and immunogen (e.g., for use as an immunization dose) is selected as that amount which induces an immunoprotective response without significant, adverse side effects. The amount will vary depending upon which specific immunogen or combination thereof is/are employed, and can vary from subject to subject, depending on a number of factors including, but not limited to, the species, age and general condition (e.g., health) of the subject, and the mode of administration. Procedures for determining the appropriate amount of immunogen administered to a subject to elicit an immune response (e.g., a protective immune response (e.g., protective immunity)) in a subject are well known to those skilled in the art.

In some embodiments, it is expected that each dose (e.g., of a composition comprising a NE and an immunogen (e.g., administered to a subject to induce an immune response (e.g., a protective immune response (e.g., protective immunity))) comprises 0.05-5000 µg of each immunogen (e.g., recombinant and/or purified protein), in some embodiments, each dose will comprise 1-500 µg, in some embodiments, each dose will comprise 350-750 µg, in some embodiments, each dose will comprise 50-200 µg, in some embodiments, each dose will comprise 25-75 µg of immunogen (e.g., recombinant and/or purified protein). In some embodiments, each dose comprises an amount of the immunogen sufficient to generate an immune response. An effective amount of the immunogen in a dose need not be quantified, as long as the amount of immunogen generates an immune response in a subject when administered to the subject. An optimal amount for a particular administration (e.g., to induce an immune response (e.g., a protective immune response (e.g., protective immunity))) can be ascertained by one of skill in the art using standard studies involving observation of antibody titers and other responses in subjects.

In some embodiments, it is expected that each dose (e.g., of a composition comprising a NE and an immunogen (e.g., administered to a subject to induce and immune response)) is from 0.001 to 15% or more (e.g., 0.001-10%, 0.5-5%, 1-3%, 2%, 6%, 10%, 15% or more) by weight immunogen (e.g., neutralized bacteria or virus, or recombinant and/or purified protein). In some embodiments, an initial or prime administration dose contains more immunogen than a subsequent boost dose In some embodiments, when a NE of the present invention is utilized to inactivate a live microorganism (e.g., virus (e.g., HIV)), it is expected that each dose (e.g., administered to a subject to induce and immune response)) comprises between 10 and $10^9$ pfu of the virus per dose; in some embodiments, each dose comprises between $10^5$ and $10^8$ pfu of the virus per dose; in some embodiments, each dose comprises between $10^3$ and $10^5$ pfu of the virus per dose; in some embodiments, each dose comprises between $10^2$ and $10^4$ pfu of the virus per dose; in some embodiments, each dose comprises 10 pfu of the virus per dose; in some embodiments, each dose comprises $10^2$ pfu of the virus per dose; and in some embodiments, each dose comprises $10^4$ pfu of the virus per dose. In some embodiments, each dose comprises more than $10^9$ pfu of the virus per dose. In some preferred embodiments, each dose comprises $10^3$ pfu of the virus per dose.

The present invention is not limited by the amount of NE used to inactivate live microorganisms (e.g., one or more types of HIV). In some embodiments, a 0.1%-5% NE solution is used, in some embodiments, a 5%-20% NE solution is used, in some embodiments, a 20% NE solution is used, and in some embodiments, a NE solution greater than 20% is used order to inactivate a pathogenic microorganism. In preferred embodiments, a 10% NE solution is used.

Similarly, the present invention is not limited by the duration of time a live microorganism is incubated in a NE of the present invention in order to become inactivated. In some embodiments, the microorganism is incubated for 1-3 hours in NE. In some embodiments, the microorganism is incubated for 3-6 hours in NE. In some embodiments, the microorganism is incubated for more than 6 hours in NE. In preferred embodiments, the microorganism is incubated for 3 hours in NE (e.g., a 10% NE solution). In some embodiments, the incubation is carried out at 37° C. In some embodiments, the incubation is carried out at a temperature greater than or less than 37° C. The present invention is also not limited by the amount of microorganism used for inactivation. The amount of microorganism may depend upon a number of factors including, but not limited to, the total amount of immunogenic composition (e.g., NE and immunogen) desired, the concentration of solution desired (e.g., prior to dilution for administration), the microorganism and the NE. In some preferred embodiments, the amount of microorganism used in an inactivation procedure is that amount that produces the desired amount of immunogen (e.g., as described herein) to be administered in a single dose (e.g., diluted from a concentrated stock) to a subject.

In some embodiments, a composition comprising a NE and an immunogen of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the NE and immunogen present in the concentrated composition. In some preferred embodiments, a subject is administered in a single dose a composition comprising 1% of the NE and immunogen present in the concentrated composition. Concentrated compositions are contemplated to be useful in a setting in which large numbers of subjects may be administered a composition of the present invention (e.g., an immunization clinic, hospital, school, etc.). In some embodiments, a composition comprising a NE and an immunogen of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eights, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

A composition comprising an immunogen of the present invention finds use where the nature of the infectious and/or disease causing agent (e.g., for which protective immunity is sought to be elicited) is known, as well as where the nature of the infectious and/or disease causing agent is unknown (e.g., in emerging disease (e.g., of pandemic proportion (e.g., influenza or other outbreaks of disease))). For example, the present invention contemplates use of the compositions of the present invention in treatment of or prevention of (e.g., via immunization with an infectious and/or disease causing HIV or HIV-like agent neutralized via a NE of the present invention) infections associated with an emergent infectious and/or disease causing agent yet to be identified (e.g., isolated and/or cultured from a diseased person but without genetic, biochemical or other characterization of the infectious and/or disease causing agent).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The formulations can be tested in vivo in a number of animal models developed for the study of mucosal and other routes of delivery. As is readily apparent, the compositions of the present invention are useful for preventing and/or treating a wide variety of diseases and infections caused by viruses, bacteria, parasites, and fungi, as well as for eliciting an immune response against a variety of antigens. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest. If polyclonal antibodies are desired, a selected mammal, (e.g., mouse, rabbit, goat, horse, etc.) can be immunized with the compositions of the present invention. The animal is usually boosted 2-6 weeks later with one or more—administrations of the antigen. Polyclonal antisera can then be obtained from the immunized animal and used according to known procedures (See, e.g., Jurgens et al., J. Chrom. 1985, 348:363-370).

In some embodiments, the present invention provides a kit comprising a composition comprising a NE and an immunogen. In some embodiments, the kit further provides a device for administering the composition. The present invention is not limited by the type of device included in the kit. In some embodiments, the device is configured for nasal application of the composition of the present invention (e.g., a nasal applicator (e.g., a syringe) or nasal inhaler or nasal mister). In some embodiments, a kit comprises a composition comprising a NE and an immunogen in a concentrated form (e.g., that can be diluted prior to administration to a subject).

In some embodiments, all kit components are present within a single container (e.g., vial or tube). In some embodiments, each kit component is located in a single container (e.g., vial or tube). In some embodiments, one or more kit component are located in a single container (e.g., vial or tube) with other components of the same kit being located in a separate container (e.g., vial or tube). In some embodiments, a kit comprises a buffer. In some embodiments, the kit further comprises instructions for use.

EXPERIMENTAL

The following examples are provided in order to demonstrate and further illustrate certain preferred embodiments and aspects of the present invention and are not to be construed as limiting the scope thereof.

Example 1

Material and Methods

Animals. Pathogen-free, female Balb/c mice (5-6 weeks old) and Hartley guinea pigs (females, 250 g) were purchased from Charles River Laboratories (Wilmington, Mass.). The mice (five to a cage) and guinea pigs (one per cage) were housed in accordance with the American Association for Accreditation of Laboratory Animal Care standards. All procedures involving animals were performed according to the University Committee on Use and Care of Animals (UCUCA) at the University of Michigan.

Reagents. Recombinant HIV $gp120_{BaL}$ and $gp120_{SF162}$ serotype proteins produced in yeast were obtained from Dr. Joseph Sodorski via Dr. David Markovitz (Harvard Medical School and University of Michigan, respectively). The 5 mg/ml aliquots of the protein solutions in a sterile saline were stored at −80° C. until used. The synthetic V3 loop peptide (BaL) was obtained from Dr. Steven King (University of Michigan). The 20-mer oligonucleotide (ODN) 5'-TCC ATG ACG TTC CGT ACG TT-3' (SEQ ID NO.: 1) (See, e.g., Moldoveanu et al., Vaccine 1998; 16(11-12): 1216-24), containing non-methylated CpG repeats, was synthesized by INTEGRATED DNA TECHNOLOGIES (IDT, Coralville, Iowa).). The S. minnesota monophosphoryl lipid A (MPL A, #L-6638), PHA-P, BSA, DTT, and other chemicals used in buffers were purchased from SIGMA-ALDRICH Corporation (St. Louis, Mo.). The saline solution, phosphate buffered saline (PBS), cell culture media, and fetal bovine serum (FBS) was purchased from GIBCO (Grand Island, N.Y.) and HYCLONE (Logan, Utah), respectively. The alkaline phosphatase (AP)-conjugated antibodies, goat anti-mouse IgG (#A-3562), goat anti-mouse IgA (α: chain specific, #A-4937) were purchased from SIGMA, and rabbit anti-guinea pig IgG was bought from ROCKLAND (#606-408).

Preparation of the gp120/adjuvant formulations. The oil-in-water nanoemulsion (NE) used in these studies obtained from NANOBIO Corporation, Ann Arbor, Mich. NE was produced by the emulsification of cetyl pyridium chloride (CPC, 1%), nonionic surfactant (5%), and ethanol (8%) in water with hot-pressed soybean oil (64%), using a high-speed emulsifier and prepared by a two-step procedure (See U.S. Pat. No. 6,015,832 to NANOBIO Corporation, Ann Arbor, Mich., hereby incorporated by reference in its entirety for all purposes). Except for the CPC, this nanoemulsion is formulated with surfactant and food substances considered 'Generally Recognized as Safe' (GRAS) by the FDA. NE mean droplet size (about 300+/−25 nm) was determined by dynamic light scattering (DLS) using the NICOMP 380 ZLS (PSS NICOMP Particle Sizing Systems, Santa Barbara, Calif.)

gp120/NE formulations were prepared by mixing gp120 protein solution with NE, using saline as diluent. Mice immunization studies were performed with a 20 μg dose of gp120 mixed with 0.1%, 0.5% and 1% NE concentrations. For immunization with immunostimulants, either 5 μg of MPL A or 10 μg CpG ODN was added to the 20 μg gp120 in 1% NE or to the 20 μg gp120 in saline. Guinea pig immunization study was performed using 50 μg dose gp120 mixed with 1% NE and saline as diluent.

Immunization procedures. Balb/c mice were immunized with two, and on one occasion with three, intranasal (i.n.) administrations of gp120/NE formulation at 3 weeks apart. The immunizations were performed by slowly applying gp120/NE mixes (10 μl per nare) to the nares of Isoflurane anesthetized mice. During delivery animals were held in the inverted position until droplets were completely inhaled. In control groups, mice were immunized with gp120 in saline, and with either NE or saline alone. Intramuscular immunization (i.m.) was performed with two doses, 3 weeks apart, of 20 µg gp120 injected in 50 µl of either saline or 1% NE. Hartley guinea pigs (3 animals per group) were anesthetized with Ketamine injection (40 mg/kg) and immunized intranasally with two i.n. administrations of gp120/NE mix (50 µl per nare) at 3 weeks apart.

Collection of blood, bronchial alveolar lavage, vaginal washes and splenocyte samples. Blood samples were obtained either from the saphenous vein, at various time points during the course of the experiment, or by cardiac puncture from euthanized premorbid mice. Serum was obtained from coagulated blood (30-60 minutes at room temperature) by centrifugation at 1500 g for 5 minutes. Collected serum samples were heat inactivated at 56° C. for 1 hour and stored at −20° C. until analyzed.

Mouse bronchial alveolar lavage fluid (BAL) was obtained from animals euthanized by inhalation of Isoflurane. The lung was infused twice with 0.5 ml of PBS with 10 µM DTT and 0.5 mg/ml aprotinin and approximately 1 ml of aspirate was recovered. BAL samples were stored at −20° C. until analyzed.

Vaginal wash samples were collected from anesthetized mice by infusion of vaginal cavities with 100 µl of PBS with 10 µM DTT and 0.5 mg/ml aprotinin. The samples were centrifugated at 10,000×g for 5 minutes at 4° C., and the supernatants were stored at −20° C. until analyzed.

Murine splenocytes were mechanically isolated from the spleens to obtain single cell suspension in PBS. The red blood cells (RBC) were removed by lysis with ACK buffer (150 mM $NH_4Cl$, 10 mM $KHCO_3$, 0.1 mM $Na_2EDTA$), and the remaining cells were washed twice in PBS. For antigen-specific proliferation or cytokine expression assays, splenocytes ($2-4 \times 10^6$ cells/ml) were resuspended in RPMI 1640 medium, supplemented with 2% FBS, L-glutamine, and penicillin/streptomycin (100 U/ml and 100 µg/ml).

Determination of anti-gp120 IgG and IgA antibodies. Mouse anti-gp120-specific IgG and IgA levels were determined by ELISA. Microtiter plates (MAXISORP; NALGE NUNC International, Rochester, N.Y.) were coated with 5 µg/ml (100 µl) of either gp120$_{BaL}$ or gp120$_{SF162}$ serotype envelope protein in the coating buffer (50 mM sodium carbonate, 50 mM sodium bicarbonate, pH 9.6) and incubated overnight at 4° C. After the protein solution was removed, plates were blocked for 30 minutes at 37° C. with PBS-1% dry milk solution. The blocking solution was aspirated and plates were used immediately or stored sealed at 4° C. until needed. Serum and BAL samples were serially diluted in 0.1% BSA in PBS, and 100 µl/well aliquots were incubated in gp120 coated plates for 1 hour at 37° C. Plates were washed three times with PBS-0.05% Tween 20, followed by 1 hour incubation with either anti-mouse IgG or anti-mouse IgA alkaline phosphatase (AP)-conjugated antibodies, then washed three times and incubated with AP substrate SIGMAFAST (SIGMA, St. Louis, Mo.) according to the manufacturer's protocol. Spectrophotometric readouts were performed using the SPECTRA MAX 340 ELISA reader (MOLECULAR DEVICES, Sunnyvale, Calif.) at 405 nm and reference wavelength of 690 nm. Endpoint antibody titers were defined as the last reciprocal serial serum dilution at which the absorption at 405 nm was greater than two times absorbance above negative control. Guinea pig anti-gp120 IgG was determined by the same method, except that rabbit anti-guinea pig IgG alkaline phosphatase (AP)-conjugate was used for detection (ROCKLAND). Antibody concentrations are presented as the mean+/−standard deviation (s.d.) of endpoint titers.

HIV-1 single-round neutralization assay. An eight strain panel of clade B HIV-1 used in this study contained the laboratory strains BaL, SF162 and MN, and primary HIV-1 isolates SS1196.01, BG1168.01, QH0692.42, 3988.25 and 5768.04 (Li 05). Virus neutralization was measured as a function of the reduction in luciferase reporter gene expression after a single round of virus infection in TZM-bl cells as described (See, e.g., Montefiori, editor. Evaluating neutralizing antibodies against HIV, SIV and SHIV in luciferase reporter gene assays. New York, N.Y.: John Wiley & Sons, 2004). The TZM-bl cells are engineered to express CD4 and CCR5 and contain integrated reporter genes for firefly luciferase and E. coli β-galactosidase under control of an HIV-1 LTR. Primary HIV-1 isolates ($TCID_{50}$, 100 to 200) were incubated with serial dilutions of sera for 1 hour at 37° C. Subsequently virus/serum mixtures were added to the 96-well flat-bottom culture plate containing adherent TZM-bl cells. Control contained cells plus virus (virus control), and cells only (background control). Bioluminescence was measured after 48 hours using BRIGHT GLO substrate solution as described by the supplier (PROMEGA, Madison, Wis.). Neutralization titers ($NT_{50}$) are the dilutions at which relative light units (RLU) were reduced by 50% compared to those of virus control wells after subtraction of background RLUs.

Proliferation assay. The proliferation of mouse splenocytes was measured by an assay of 5-bromo-2-deoxyuridine (BrdU) incorporation using a commercially available labeling and detection kit (Cell Proliferation ELISA, ROCHE Molecular Biochemicals, Mannheim, Germany). To assess antigen specific proliferation, cells ($2 \times 10^6$ cell/ml) were incubated in medium alone and the presence of gp120$_{BaL}$ (5 µg/ml), or as control with a PHA-P (2 µg/ml), for 48 hours and then pulsed with BrdU for 24 hours. Cell proliferation was measured according to the manufacturer's instructions using SPECTRA MAX 340 ELISA Reader (MOLECULAR DEVICES, Sunnyvale, Calif.) at 370 nm and reference wavelength of 492 nm.

Analysis of cytokine expression in vitro. Mouse splenocytes were seeded at $4 \times 10^6$ cells/ml (RPMI 1640, 2% FBS) and incubated with either gp120$_{BaL}$, gp120$_{SF162}$ (5 µg/ml) or with V3 loop peptide (20 nM) for 72 hours at 37° C. Cell culture supernatants were harvested and analyzed for the presence of cytokines. The cytokine assays were performed using QUANTIKINE ELISA kits (R&D SYSTEMS, Inc., Minneapolis, Minn.) according to the manufacturer's instructions.

Statistical Analysis. Statistical analysis of the results was preformed using ANOVA, and Student's T-test for the determination of the p value.

Example 2

Nasal Immunization with Recombinant HIV gp120 Protein Mixed with Nanoemulsion Induces Potent IgG Response in Serum In order to determine whether NE has an adjuvant activity in the mucosal immunization with a recombinant HIV gp120 protein, Balb/c mice were intranasally (i.n.) immunized with either gp120$_{BaL}$ or gp120$_{SF162}$ serotype of antigen. Effect of NE concentration was assessed using 20 μg of gp120$_{BaL}$ in saline or mixed with a 0.1%, 0.5% and 1% range of NE concentrations. Blood was collected at 6 weeks after two immunizations and at 12 weeks after three immunizations and analyzed for gp120-specific antibodies by ELISA. All mice immunized with either of gp120$_{BaL}$/NE preparations were seropositive after only two immunizations. The anti-gp120$_{BaL}$ IgG response showed concentration-dependent effect of NE, with lowest titers in gp120$_{BaL}$/0.1% NE and highest in gp120$_{BaL}$/1% NE immunization groups (mean titers of $1.3\times10^4$ and $2.6\times10^5$, respectively). Mice immunized with gp120$_{BaL}$/saline did not have detectable anti-gp120$_{BaL}$ antibodies. Serum anti-gp120 IgG titers after i.n. immunization with either 0.5% or 1% NE were comparable, or even higher, than antibody response after two i.m. injections with gp120$_{BaL}$ in saline or mixed with 1% NE. A third i.n. immunization did not significantly increase antibody titers in either of the immunization groups (See FIG. 1A). Thus, the present invention provides that only two i.n. administrations of gp120$_{BaL}$ with NE adjuvant are required to mount a potent systemic IgG response in mice.

Figure 1B:
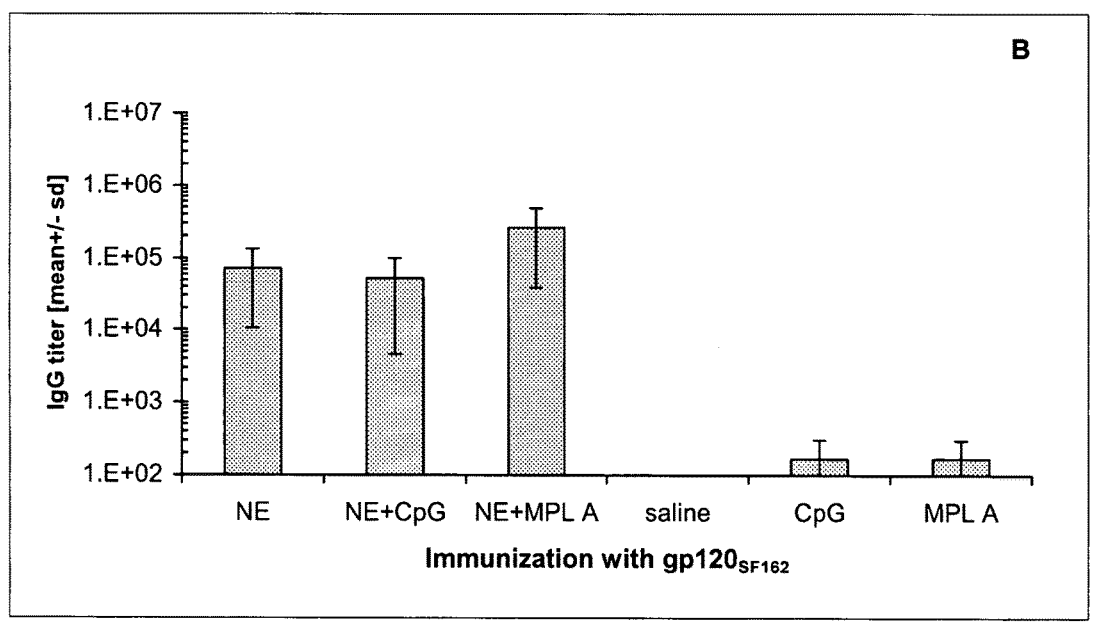

NE is sufficient for robust mucosal adjuvanation. NE-produced immune responses were compared with the effects of known immunostimulants, unmethylated CpG ODN and MPL A. Mice were i.n. immunized with 20 μg gp120$_{SF162}$ mixed with 1% NE (gp120$_{SF162}$/NE) and compared to immunization with antigen mixed with either CpG ODN (gp120$_{SF162}$/CpG) or with MPL A (gp120$_{SF162}$/MPL A). In order to investigate the effect of combining the NE with immunostimulants, mice were immunized with a gp120$_{SF162}$/NE and additionally with either CpG (gp120$_{SF162}$/NE+CpG) or MPL A (gp120$_{SF162}$/NE+MPL A). Similar to immunization with gp120$_{Bal}$, mice immunized with gp120$_{SF162}$/NE responded with high anti-gp120$_{SF162}$ IgG titers. Combination of NE with MPL A (but not with CpG) resulted in a modest increase in mean antibody titer (2 to 3 fold over immunization with gp120$_{SF162}$/NE alone), however the difference was not statistically significant ($p>0.05$). In contrast, immunizations with antigen mixed with either CpG or MPL A alone produced only weak immune response (See FIG. 1B).

Example 3

Figure 1C:
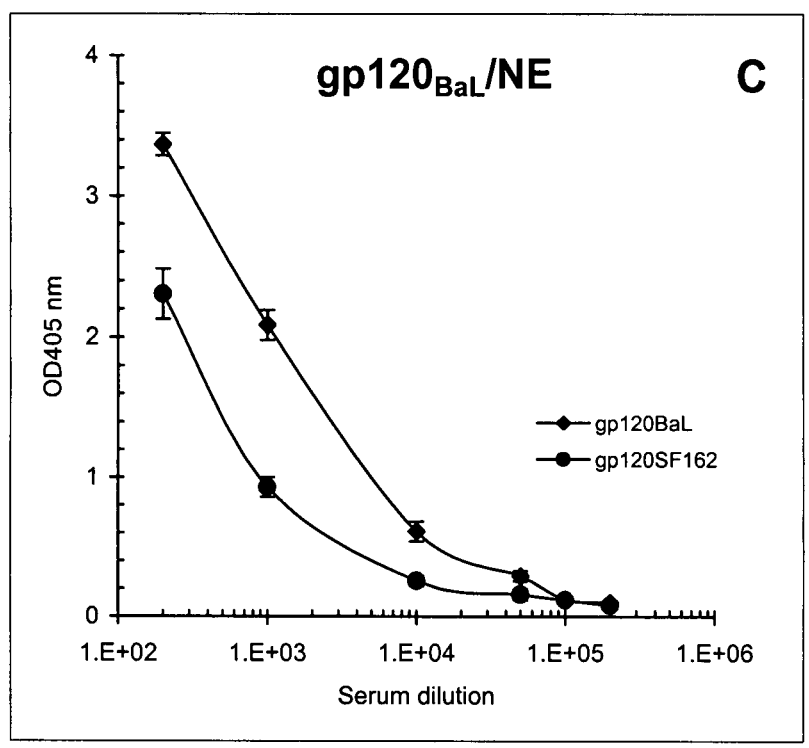
Figure 1D:
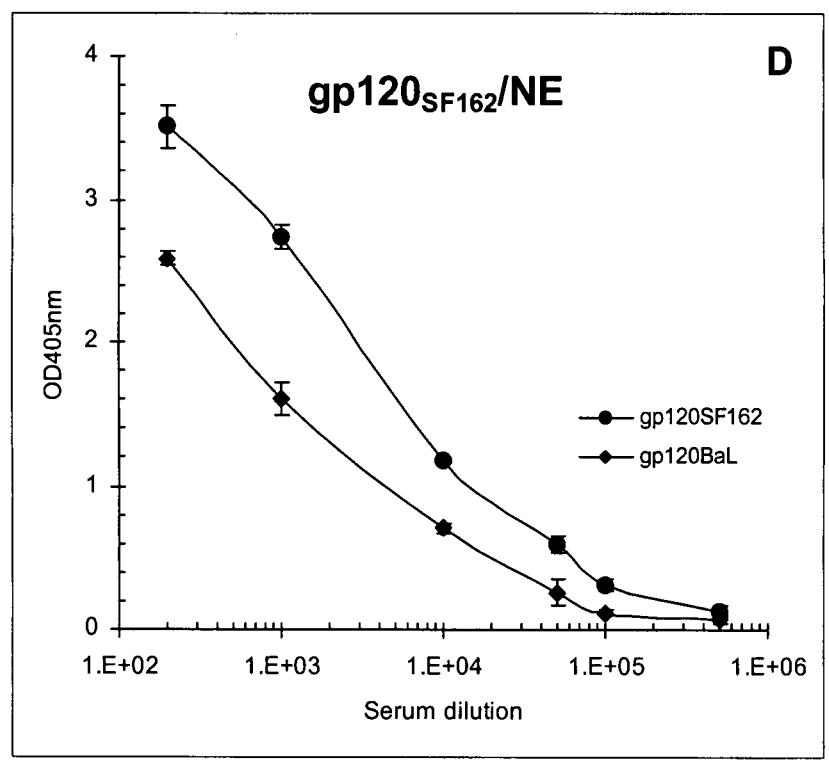

Antibodies Generated Against One Serotype of gp120 Cross-React with Other gp120 Serotypes Experiments conducted during the development of the present invention determined that i.n. immunization with either serotype of gp120 protein produced highly cross-reacting IgG antibodies. For example, the IgG antibody raised against either gp120$_{BaL}$ or gp120$_{SF162}$ cross-reacted with a heterologous serotype with activity that was comparable with binding to autologous envelope protein (See FIGS. 1C and 1D). Thus, the present invention provides that mucosal immunization with either serotype of gp120 can induce comparable immune responses. Thus, in some embodiments, NE adjuvant can produce a repertoire of IgG capable of recognizing both variable and conserved epitopes of the gp120 immunogen (e.g., that participate in protective immunity against various types of HIV-1 (See, e.g., Mascola, Curr Mol Med 2003; 3(3):209-16).

Example 4

Figure 2A:
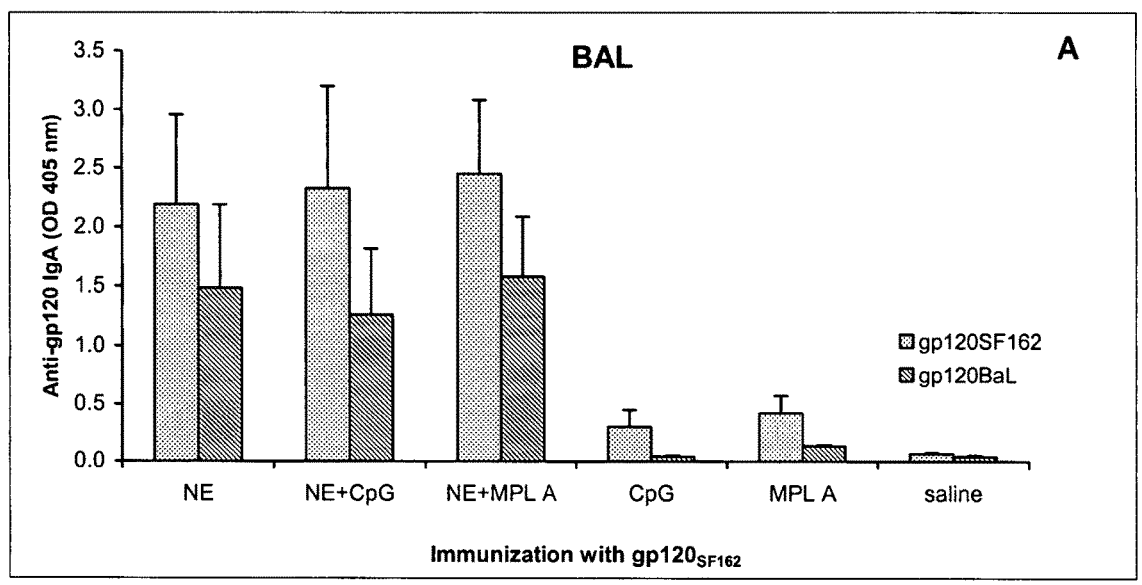
Figure 2B:
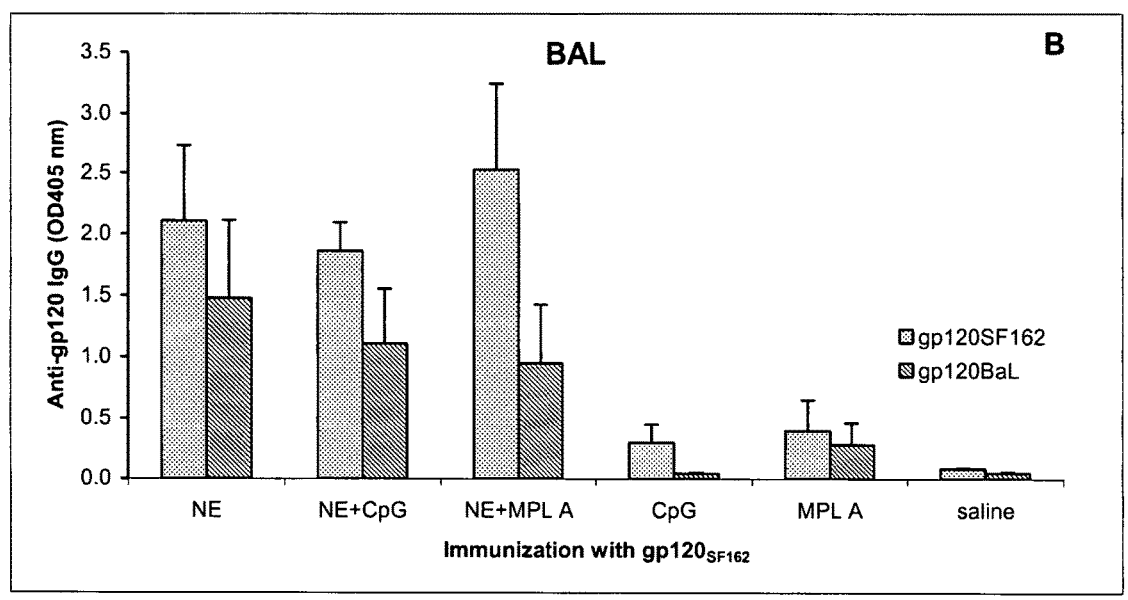
Figure 2C:
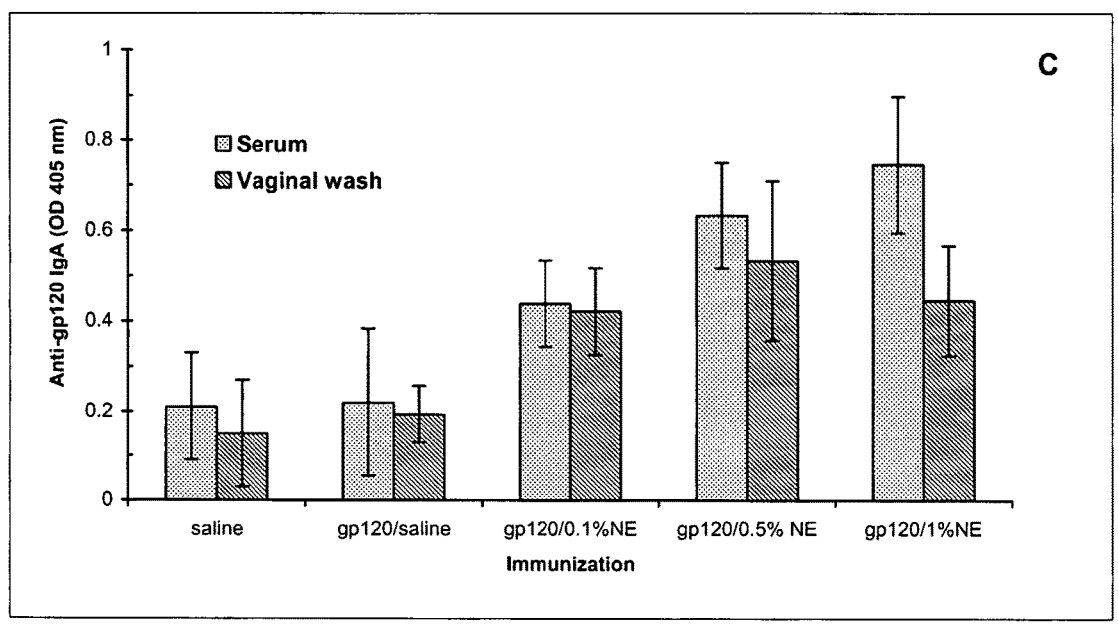

Nasal Administration of pg120/NE Generates Anti-gp120 Specific IgA Antibodies Detectable in Bronchial and Vaginal Mucosal Surfaces BAL fluids, vaginal washes and sera were analyzed for the assessment of mucosal response. Mice i.n. immunized with gp120$_{SF162}$/NE had significant levels of gp120$_{SF162}$-specific secretory IgA and IgG antibodies in BAL fluid (See FIGS. 2A and 2B). Similar to serum, both IgA and IgG antibodies demonstrated cross-reactivity with heterologous gp120$_{BaL}$ immunogen. Anti-gp120$_{BaL}$ IgA antibodies were also detected in serum and distant mucosal sites (e.g., as measured in vaginal wash samples (See FIG. 2C)). Immunization with either type of gp120 in saline failed to produce mucosal IgA and IgG responses detectable in the BAL, serum, and vaginal secretions. Thus, the present invention provides that significant mucosal responses, both locally (e.g., in bronchial mucosa) and in distant sites (e.g., vaginal secretions), can be induced in response to i.n. immunization with antigen (e.g., gp120) delivered with NE adjuvant.

Example 5

Cell Mediated Immune Responses

Figure 3A:
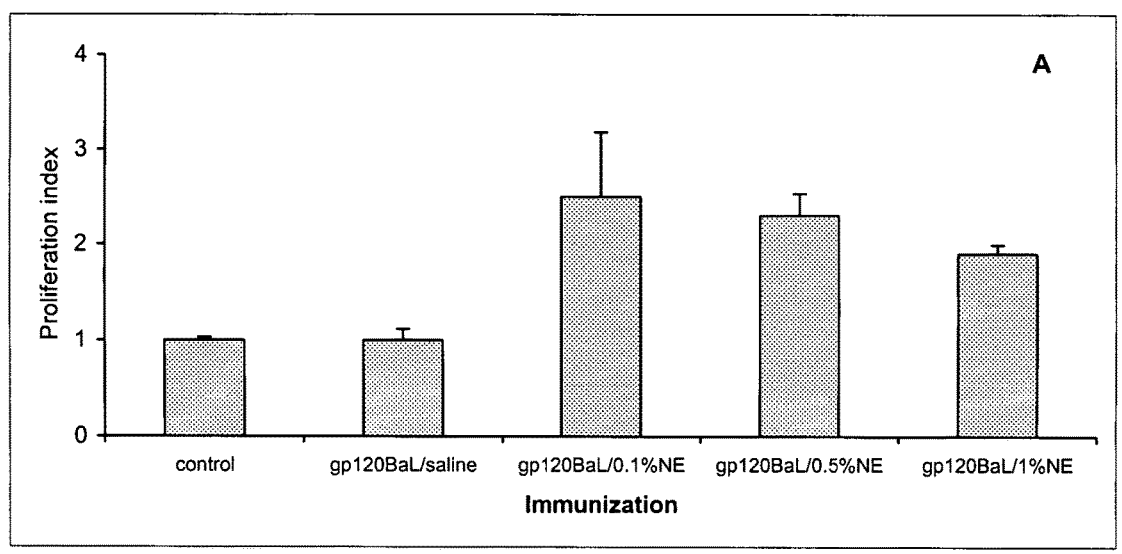
Figure 3B:
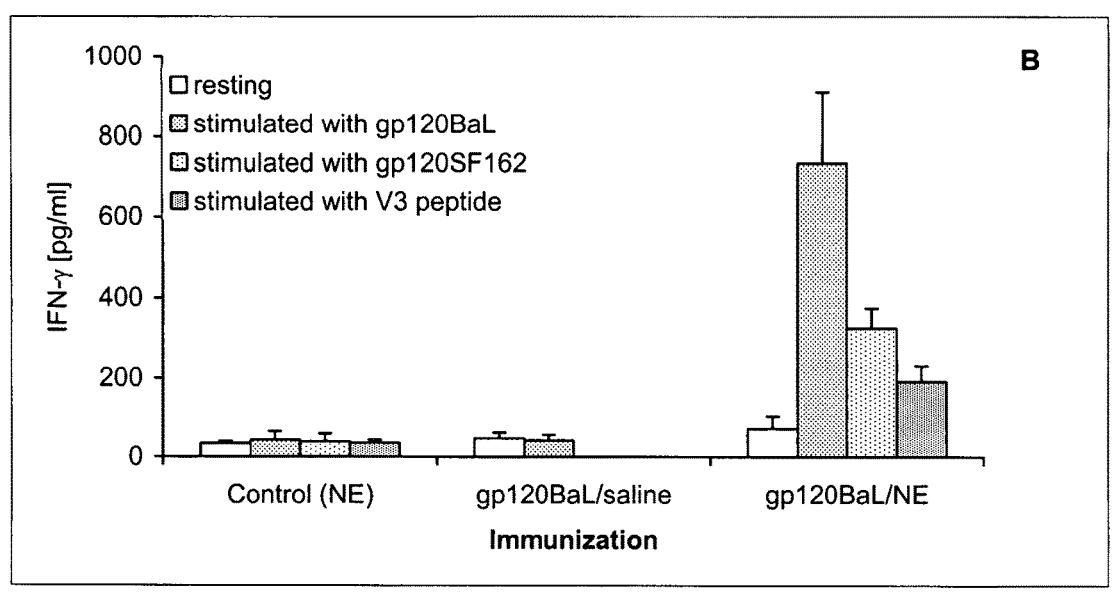

Cellular immune responses were assessed in vitro by antigen-specific T-cell proliferation assays as well as characterization of T helper-type cytokine production. Antigen specific proliferative responses were detected in re-stimulated splenic lymphocytes from animals immunized with the gp120$_{BaL}$/NE but were absent in either mice immunized with gp120$_{BaL}$/saline or with control animals (treated with saline or NE alone) (See FIG. 3A). Intranasal immunization with gp120$_{BaL}$/NE produced strong cell-mediated immune responses as measured by splenic IFN-γ production (See FIG. 3B). In vitro stimulation with either gp120$_{BaL}$ or gp120$_{SF162}$ serotypes produced high IFN-γ responses to both autologous (BaL) and heterologous (SF162) types of gp120. A substantial induction of IFN-γ was also obtained with an oligopeptide fragment of the V3 loop, indicating the presence of CTLs specific for the dominant epitope involved in virus binding and neutralization (See, e.g., Kwong et al., Nature 1998; 393(6686):648-59; Takahashi et al., Science 1992; 255(5042):333-6). Antigen-specific induction or IFN-γ and the lack of detectable IL-4 expression evidences Th1 polarization of the cellular immune response. No significant cytokine expression was detected in splenocytes from control mice or from mice immunized with gp120$_{BaL}$ in saline.

Example 6

Immunization with gp120/NE Induces HIV-1 Neutralizing Antibodies

Figure 4A:
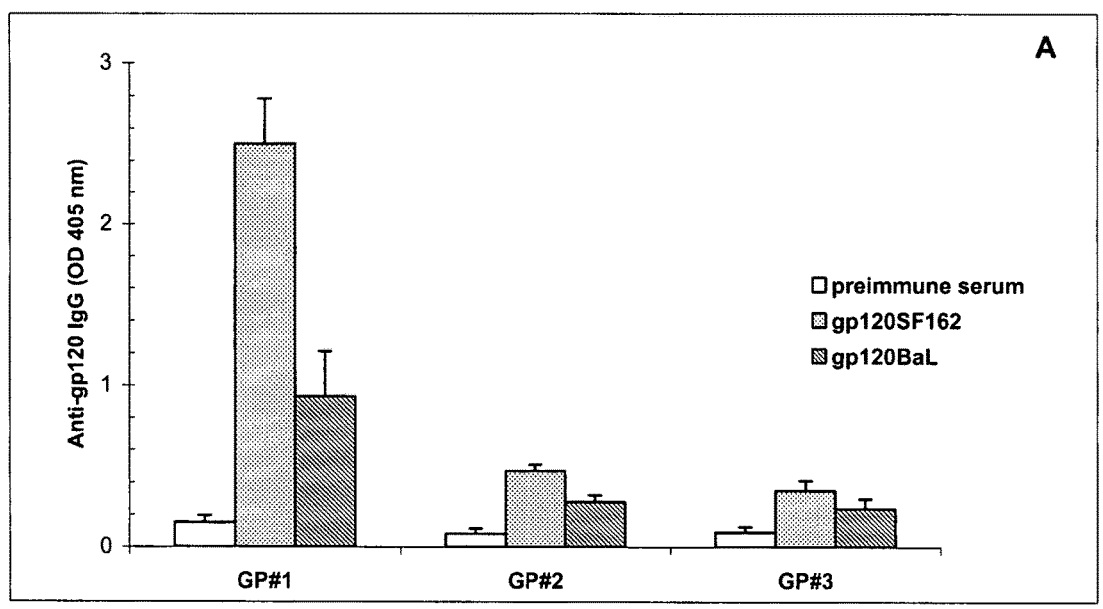
Figure 4B:
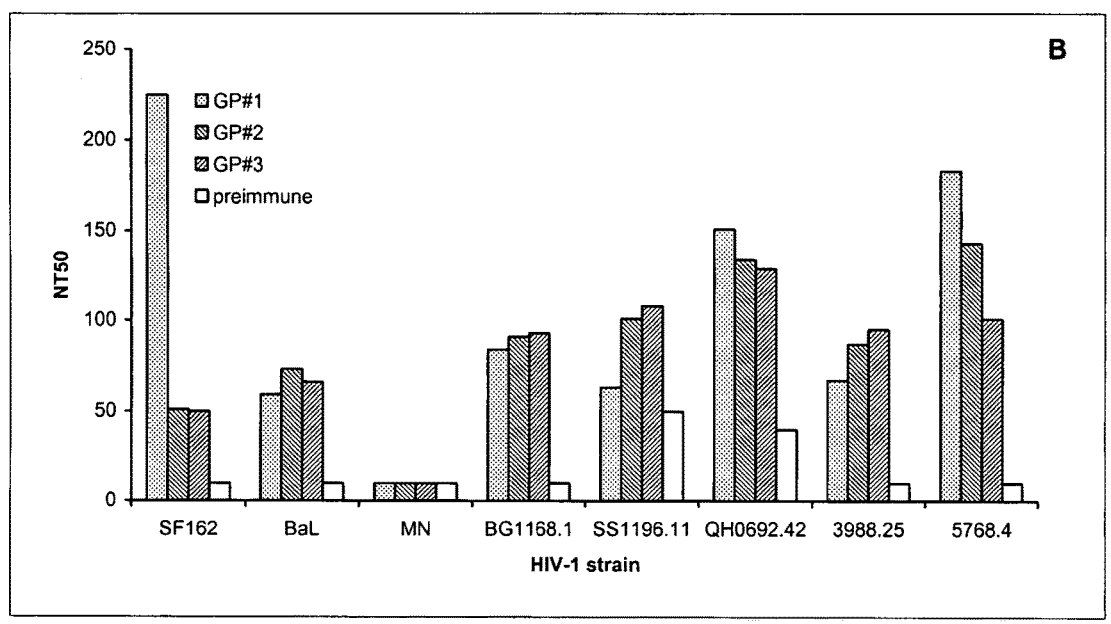

In order to characterize potential neutralizing activity of gp120-specific antibodies induced by mucosal immunization, guinea pigs were administered with two doses of gp120$_{SF162}$ mixed with 1% NE. Immunization produced significant, albeit varied, levels of serum anti-gp120 IgG antibodies in individual animals (See FIG. 4A). As observed in mice, the guinea pig anti-gp120 IgG cross-reacted with heterologous gp120 immunogen. Immune sera from guinea pigs were tested for neutralizing activity against HIV-1. The breadth of the neutralizing response was evaluated in a panel of 8 viruses, including 3 laboratory strains and 5 primary HIV isolates. The highest neutralizing titer ($NT_{50}$) toward autologous M-tropic strain of $HIV_{SF162}$ was detected in serum from the most responsive animal ($NT_{50}$=225) (See FIG. 4B). However, significant neutralizing activity ($NT_{50}$>50) was also detected in two other animals, despite much lower anti-gp120 IgG levels.

Neutralization of heterologous M-tropic strain $HIV_{BaL}$ was comparable in all guinea pigs with $NT_{50}$ greater than 50. No neutralization was observed with laboratory strain of T-tropic $HIV_{MN}$ virus. All five primary HIV isolates tested were effectively neutralized with sera from vaccinated guinea pigs. Neutralizing activity for the primary HIV isolates was comparable with both laboratory strains. The $NT_{50}$ values for BG1168.1, SS1196.11 and 3988.25 ranged from 50 to 100 depending on the serum. The isolates QH0692.42 and 5768.4 were effectively neutralized with $NT_{50}$ values grater than 100.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of inducing a human immunodeficiency virus (HIV) specific immune response in a subject comprising nasally administering to the subject an effective amount of an immunogenic composition comprising a nanoemulsion and an immunogen, wherein the immunogen comprises recombinant gp120 and wherein the nanoemulsion comprises oil, ethanol, TWEEN 20 or TWEEN 80, cetylpyridinium chloride and water, to generate a HIV specific immune response comprising generation of broadly reactive gp120-specific antibodies with HIV-neutralizing activity.

2. The method of claim 1, wherein the gp120-specific antibodies with HIV-neutralizing activity display neutralizing activity against three or more primary HIV isolates selected from the group consisting of BG1168.1, SS1196.11, 3988.25, QH0692.42 and 5768.4.

3. The method of claim 1, wherein the gp120-specific antibodies with HIV-neutralizing activity display neutralizing activity against four or more primary HIV isolates selected from the group consisting of BG1168.1, SS1196.11, 3988.25, QH0692.42 and 5768.4.

4. The method of claim 1, wherein the gp120-specific antibodies with HIV-neutralizing activity display neutralizing activity against HIV isolates BG1168.1, SS1196.11, 3988.25, QH0692.42 and 5768.4.

5. The method of claim 4, wherein the gp120-specific antibodies with HIV-neutralizing activity are detectable in bronchial and vaginal mucosal surfaces in the subject.

6. The method of claim 1, wherein the immune response comprises generation of a Th1 type cellular immune response against both autologous and heterologous gp120.

7. The method of claim 6, wherein the Th1 type cellular immune response comprises generation of a level of IFN-γ that is at least ten fold greater than the level of IFN-γ generated in a control subject administered an equal amount of recombinant gp120 suspended in saline.

8. The method of claim 1, wherein the immune response comprises a systemic IgG response to the HIV.

9. The method of claim 8, wherein the systemic IgG response comprises generation of a gp120-specific IgG antibody titer that is at least two fold greater than the gp120-specific IgG antibody titer generated in a control subject administered an equal amount of recombinant gp120 suspended in saline.

10. The method of claim 8, wherein the systemic IgG response comprises generation of a gp120-specific IgG antibody titer that is at least 100fold greater than the gp120-specific IgG antibody titer generated in a control subject administered an equal amount of recombinant gp120 suspended in saline.

11. The method of claim 8, wherein the systemic IgG response comprises generation of a gp120-specific IgG antibody titer that is at least 1000fold greater than the gp120-specific IgG antibody titer generated in a control subject administered an equal amount of recombinant gp120 suspended in saline.

12. The method of claim 1, wherein the immune response comprises a mucosal IgA response to the HIV.

13. The method of claim 1, wherein the immunogenic composition comprises between 15 and 75 μg of recombinant gp120.

14. The method of claim 1, wherein the immunogenic composition comprises 0.1 - 20% nanoemulsion solution.

15. The method of claim 1, wherein the nanoemulsion has a mean droplet size of about 200-800 nanometers.

* * * * *

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
tccatgacgt tccgtacgtt                                               20
```